US011112410B2

United States Patent

(12) United States Patent
Kang et al.

(10) Patent No.: US 11,112,410 B2
(45) Date of Patent: Sep. 7, 2021

(54) METHODS FOR CAPTURING, ISOLATION, AND TARGETING OF CIRCULATING TUMOR CELLS AND DIAGNOSTIC AND THERAPEUTIC APPLICATIONS THEREOF

(71) Applicant: PRESIDENT AND FELLOWS OF HARVARD COLLEGE, Cambridge, MA (US)

(72) Inventors: Joo-Hun Kang, Boston, MA (US); Donald E. Ingber, Boston, MA (US); Michael Super, Lexington, MA (US); Alexander L. Watters, North Andover, MA (US); Harry Scott Driscoll, Allston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 73 days.

(21) Appl. No.: 16/092,288

(22) PCT Filed: Apr. 10, 2017

(86) PCT No.: PCT/US2017/026768
§ 371 (c)(1),
(2) Date: Oct. 9, 2018

(87) PCT Pub. No.: WO2017/180499
PCT Pub. Date: Oct. 19, 2017

(65) Prior Publication Data

US 2019/0145980 A1 May 16, 2019

Related U.S. Application Data

(60) Provisional application No. 62/321,859, filed on Apr. 13, 2016, provisional application No. 62/324,738, filed on Apr. 19, 2016.

(51) Int. Cl.

| | |
|---|---|
| ***A61K 39/00*** | (2006.01) |
| ***G01N 33/574*** | (2006.01) |
| ***A61K 47/64*** | (2017.01) |

(52) U.S. Cl.
CPC .... *G01N 33/57492* (2013.01); *A61K 39/0011* (2013.01); *A61K 47/6415* (2017.08); *G01N 2333/4724* (2013.01); *G01N 2333/4725* (2013.01); *G01N 2333/705* (2013.01); *G01N 2333/71* (2013.01); *G01N 2400/00* (2013.01); *G01N 2800/52* (2013.01)

(58) Field of Classification Search
CPC .............................................. G01N 33/57492
USPC .................................................... 424/277.1
See application file for complete search history.

(56) References Cited

U.S. PATENT DOCUMENTS

| | | | | |
|---|---|---|---|---|
| 2008/0166379 A1* | 7/2008 | Lawman | A61K 39/0011 424/277.1 |
| 2014/0162281 A1* | 6/2014 | Han | G01N 1/34 435/7.1 |

FOREIGN PATENT DOCUMENTS

| | | |
|---|---|---|
| EP | 1056544 B1 | 9/2005 |
| KR | 10-2007-0119785 A | 12/2007 |
| WO | 2013/126774 A2 | 8/2013 |

OTHER PUBLICATIONS

Vickers et al (Biomed Microdevices, 2011, 13: 565-571).*
Maheswaran et al (NEJM, 2008, 359: 366-377).*
Muto et al (Biol Pharm Bull, 1999, 22(4): 347-352).*
Wang et al (Curr Colorectal Cancer Rep, 2013, 9: 303-311).*
Kang et al (Lab Chip, 2012, 12: 2175-2181).*
Cancino-Bernardi et al. "Detection of leukemic cells by using jacalin as the biorecognition layer: A new strategy for the detection of circulating tumor cells." ChemElectroChem 2(7):963-969 (2015).
Kang et al. "An extracorporeal blood-cleansing device for sepsis therapy." Nature Medicine 20(10):1211-1216 (2014).
Ma et al., "Ficolin-1-PTX3 complex formation promotes clearance of altered self-cells and modulates IL-8 production." The Journal of Immunology 191(3):1324-1333 (2013).
Moon et al., "Continuous separation of breast cancer cells from blood samples using multi-orifice flow fractionation (MOFF) and dielectrophoresis (DEP)." Lab on a Chip 11(6):1118-1128 (2011).
Muller et al. "Circulating tumor cells in breast cancer: correlation to bone marrow micrometastases, heterogeneous response to systemic therapy and low proliferative activity." Clinical Cancer Research 11(10):3678-3685 (2005).
Myung et al., "Microfluidic devices to enrich and isolate circulating tumor cells." Lab on a Chip 15(24):4500-4511 (2015).
Nagrath et al., "Isolation of rare circulating tumour cells in cancer patients by microchip technology." Nature 450(7173):1235-1239 (2007).
Ramadan et al., "Magnetic-based microfluidic platform for biomolecular separation." Biomedical Microdevices 8(2):151-158 (2006).
Scher et al. "Circulating tumour cells as prognostic markers in progressive, castration-resistant prostate cancer: a reanalysis of IMMC38 trial data." The Lancet Oncology 10(3):233-239 (2009).
Singh et al., "Long circulating lectin conjugated paclitaxel loaded magnetic nanoparticles: a new theranostic avenue for leukemia therapy." PLoS One 6(11):e26803 (2011).

(Continued)

*Primary Examiner* — Sean E Aeder
(74) *Attorney, Agent, or Firm* — Nixon Peabody LLP; David S. Resnick; Nicole D. Kling

(57) ABSTRACT

The invention relates to methods of detection, capture, isolation and targeting of cancer cells for example circulating tumor cells (CTCs) using carbohydrate recognition domain of a lectin. The invention relates to methods of diagnosis, prognosis and treatment of cancer.

19 Claims, 9 Drawing Sheets

Specification includes a Sequence Listing.

(56) References Cited

OTHER PUBLICATIONS

Xia et al., "Combined microfluidic-micromagnetic separation of living cells in continuous flow." Biomedical Microdevices 8(4):299-308 (2006).

Breiman et al. "Carcinoma-associated fucosylated antigens are markers of the epithelial state and can contribute to cell adhesion through CLEC17A (Prolectin)." Oncotarget 7(12): 14064-14082 (2016).

* cited by examiner

*FIG. 8*

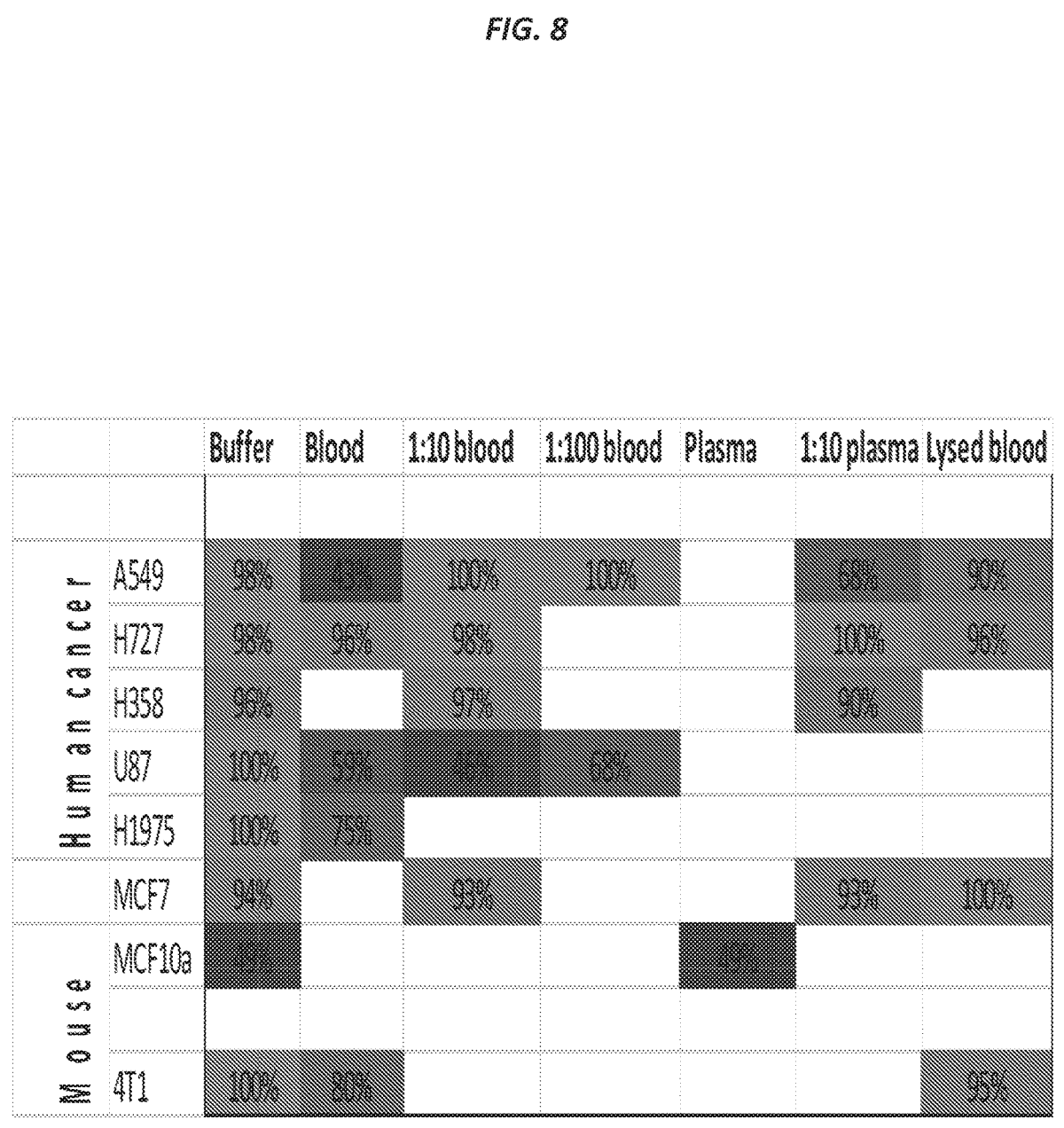

| | | Buffer | Blood | 1:10 blood | 1:100 blood | Plasma | 1:10 plasma | Lysed blood |
|---|---|---|---|---|---|---|---|---|
| | | | | | | | | |
| Human cancer | A549 | 98% | [illegible] | 100% | 100% | | 68% | 90% |
| | H727 | 98% | 96% | 98% | | | 100% | 96% |
| | H358 | 96% | | 97% | | | 90% | |
| | U87 | 100% | 55% | [illegible] | 68% | | | |
| | H1975 | 100% | 75% | | | | | |
| | MCF7 | 94% | | 93% | | | 93% | 100% |
| Mouse | MCF10a | [illegible] | | | | [illegible] | | |
| | | | | | | | | |
| | 4T1 | 100% | 80% | | | | | 95% |

SEQUENCE LISTING

```
<160> NUMBER OF SEQ ID NOS: 3

<210> SEQ ID NO 1
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245


<210> SEQ ID NO 2
<211> LENGTH: 228
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 2

Glu Thr Val Thr Cys Glu Asp Ala Gln Lys Thr Cys Pro Ala Val Ile
1 5 10 15

Ala Cys Ser Ser Pro Gly Ile Asn Gly Phe Pro Gly Lys Asp Gly Arg
20 25 30

Asp Gly Thr Lys Gly Glu Lys Gly Glu Pro Gly Gln Gly Leu Arg Gly
35 40 45

Leu Gln Gly Pro Pro Gly Lys Leu Gly Pro Pro Gly Asn Pro Gly Pro
50 55 60

Ser Gly Ser Pro Gly Pro Lys Gly Gln Lys Gly Asp Pro Gly Lys Ser
65 70 75 80

Pro Asp Gly Asp Ser Ser Leu Ala Ala Ser Glu Arg Lys Ala Leu Gln
85 90 95

Thr Glu Met Ala Arg Ile Lys Lys Trp Leu Thr Phe Ser Leu Gly Lys
100 105 110

Gln Val Gly Asn Lys Phe Phe Leu Thr Asn Gly Glu Ile Met Thr Phe
115 120 125

Glu Lys Val Lys Ala Leu Cys Val Lys Phe Gln Ala Ser Val Ala Thr
130 135 140

Pro Arg Asn Ala Ala Glu Asn Gly Ala Ile Gln Asn Leu Ile Lys Glu
145 150 155 160

Glu Ala Phe Leu Gly Ile Thr Asp Glu Lys Thr Glu Gly Gln Phe Val
165 170 175

Asp Leu Thr Gly Asn Arg Leu Thr Tyr Thr Asn Trp Asn Glu Gly Glu
180 185 190

Pro Asn Asn Ala Gly Ser Asp Glu Asp Cys Val Leu Leu Leu Lys Asn
195 200 205

Gly Gln Trp Asn Asp Val Pro Cys Ser Thr Ser His Leu Ala Val Cys
210 215 220

Glu Phe Pro Ile
225

<210> SEQ ID NO 3
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

Val Gly Asn Lys Phe Phe Leu Thr Asn Gly Glu Ile Met Thr Phe Glu
1 5 10 15

Lys Val Lys Ala Leu Cys Val Lys Phe Gln Ala Ser Val Ala Thr Pro
20 25 30

Arg Asn Ala Ala Glu Asn Gly Ala Ile Gln Asn Leu Ile Lys Glu Glu
35 40 45

Ala Phe Leu Gly Ile Thr Asp Glu Lys Thr Glu Gly Gln Phe Val Asp
50 55 60

Leu Thr Gly Asn Arg Leu Thr Tyr Thr Asn Trp Asn Glu Gly Glu Pro
65 70 75 80

Asn Asn Ala Gly Ser Asp Glu Asp Cys Val Leu Leu Leu Lys Asn Gly
85 90 95

-continued

```
Gln Trp Asn Asp Val Pro Cys Ser Thr Ser His Leu Ala Val Cys Glu
            100                 105                 110

Phe Pro Ile
        115
```

METHODS FOR CAPTURING, ISOLATION, AND TARGETING OF CIRCULATING TUMOR CELLS AND DIAGNOSTIC AND THERAPEUTIC APPLICATIONS THEREOF

CROSS-REFERENCE TO RELATED APPLICATIONS

This application is a 35 U.S.C. § 371 National Phase Entry Application of International Application No. PCT/US2017/026768 filed Apr. 10, 2017, which designates the U.S. and claims benefit under 35 U.S.C. § 119(e) of U.S. Provisional Application No. 62/321,859 filed Apr. 13, 2016 and 62/324,738 filed Apr. 19, 2016, the contents of which are incorporated herein by reference in their entireties.

GOVERNMENT SUPPORT

This invention was made with government support under N66001-11-1-4180 awarded by U.S. Department of Defense—Defense Advanced Research Projects Agency. The government has certain rights in the invention.

SEQUENCE LISTING

The instant application contains a Sequence Listing which has been submitted electronically in ASCII format and is hereby incorporated by reference in its entirety. Said ASCII copy, created on Apr. 5, 2017, is named 002806-086332-PCT_SL.txt and is 5,901 bytes in size.

TECHNICAL FIELD

The technology disclosed herein relates to methods, molecules, compositions and kits for detecting, capturing, isolating and targeting of tumor cells. The technology relates to methods for detection, prognosis, diagnosis and therapeutics of cancer.

BACKGROUND

Circulating tumor cells (CTCs) released from primary tumor tissues into the bloodstream or lymphatic vessels are able to colonize distant organs giving rise to metastasis and thus play a crucial role in tumor dissemination and progression (Baccelli, I. et al., 2013). Detection and enumeration of CTCs is beneficial for early metastasis detection and provides prognostic and diagnostic information (Scher, H I. et al., 2009). (Müller, V. et al., 2005). Therefore detection, separation and enumeration of CTCs is relevant to understand molecular drivers of cancer and metastasis and improving prognosis and therapeutic strategies of metastatic cancers.

The most commonly used technique for CTC isolation is antibody-based isolation by targeting the epithelial-specific markers or tumor specific antigens present of the surface of CTCs. False positive selection may occur due to expression of epithelial markers in non-epithelial cells (Man, Y. et al., 2011). However, detection and isolation of CTCs is also hampered by their low numbers and the heterogeneity of CTCs, including subpopulations which have lost the characteristic epithelial features due to the process of Epithelial-mesenchymal transition (EMT). EMT is regarded as a pivotal process in tumor metastasis, leading to dedifferentiation and increased mobility of cancer cells and eventually loss of cell adhesion and therefore plays an important role in tumor local invasion and subsequent dissemination. Current isolation technologies used for CTC capture that are based on epithelial surface markers, such as Epithelial Cell Adhesion Molecule (EpCam), could miss metastatic tumor cells circulating in blood (Alix-Panabieres, C. & Pantel, K., 2013). Among the EpCAM-based technologies, the CellSearch CTC test has gained considerable attention and is the only diagnostic test that is currently approved by the US Food and Drug Administration for the automated detection and enumeration of circulating tumor cells (Food and Drug Administration, 2004). However, EpCAM is not a perfect marker for CTC selection due to the high variation in its gene expression between tumor subtypes, its transcription in leukocytes, and loss of expression during EMT (Soysal, S. D. et al., 2013) (Gorges. T. M. et al., 2012). One approach to address the concern of variable EpCAM expression, is the use of EpCAM in addition to tumor type-specific antigens, such as MUC1 for breast and colon cancer or PSA for prostate cancer (Gold, B. et al., 2015); however, expression of these markers also vary between tumor cells of the same type, and there are no known specific antigens for most types of cancer cells. Recently, studies have suggested that EMT markers also could be used for the detection or capture of CTCs (Yu, M. et al., 2013). Strategies are employed using a combination of two or three markers to increase the number of isolated CTCs and decrease false positives. Stem cell markers and EMT markers have been used (Wu, S. et al., 2015). Some technologies, such as the AdnaTest technology, use a mix of antibodies directed towards various tumor-cell associated antigens during the enrichment step. (Visit: http://www.adnagen.com/). However, a single marker which can overcome the limitations posed by existing CTC capture approaches, or enhance CTC capture when used in combination with those approaches, has not yet been identified. As such there is an unmet need for methods of CTC detection and isolation that overcome the limitations of current techniques by targeting surface molecules are that are specific to broad range of cancer cells, but not normal cells, and that remain on the surfaces of epithelial tumor cells even after they undergo an EMT.

SUMMARY

Described herein are methods, compositions and kits for detection, capture and isolation of circulating tumor cells (CTCs) and applications thereof. It is contemplated that the methods, compositions and kits disclosed herein also can be used to detect, capture and isolate cellular components of CTCs, for example, cell membrane and or secreted components of CTCs, including extracellular vesicles, exosomes, microvesicles and the like. In one aspect, the present invention provides for use of cell surface carbohydrate-binding proteins for example lectins, for detection, capture and isolation of cancer cells, preferably CTCs.

Accordingly in one aspect, the technology disclosed herein relates to a method for capturing circulating tumor cells (CTCs) from biological fluids of a subject, comprising contacting the biological fluid with a lectin molecule attached to a surface. In some embodiments, the surface to which the lectin molecule is attached can be bead, hollow fiber, porous scaffold, particle or well. In some embodiments, the surface is magnetic. In some embodiments, the method further comprises isolation of the captured CTCs, e.g., by passing the biological fluid containing captured CTCs through a microfluidic magnetic separation device.

In some embodiments, the CTCs of the present invention express mannose-containing carbohydrates, known as mannans, on their surfaces.

In some embodiments, the biological fluid is selected from is selected from a body fluid, such as whole blood, plasma, any cell-containing blood fraction, cerebrospinal fluid, bone marrow, a cell sample (e.g., stem cells), joint fluid, urine, tears or feces.

In some embodiments, the biological fluid, e.g., bone marrow, is to be used in transplantation. The transplantation can be autologous or allogeneic.

In some embodiments, the lectin molecule contains a carbohydrate recognition domain, e.g., collectin carbohydrate recognition domain of a collectin, carbohydrate recognition domain of a mannose binding lectin. In some embodiments the lectin molecule is a mannose binding lectin, ficolin, dectin, C-type lectin, fucose-binding lectin, hemopexin, S-type lectin, Galectin. In some embodiments, the lectin molecule is an engineered molecule, for e.g., FcMBL. In some embodiments, the lectin molecule is of mammalian origin, for e.g. human origin. In some embodiments, the lectin molecule comprises at least 80% amino acid sequence identity to human lectin and retains at least 80% of its biological ability.

In another aspect, described herein is a method of analyzing a CTC captured from a sample by the methods described, wherein analyses of the captured CTCs can comprise an immunochemical analysis, morphological analysis, genomics analysis, epigenomics analysis, metabolomics analysis, transcriptomics analysis, proteomics analysis, DNA mutation analysis, whole genome analysis, protein and/or RNA expression level of a specific gene or a combination thereof. In some embodiments, the analysis is used to assess a risk of developing a metastatic tumor in the patient carrying or having carried a tumor. In some embodiments, the CTC is captured for analysis from a sample e.g., whole blood, body fluid, any cell-containing blood fraction, a fragmented tumor, a biopsy, aspirate, a tumor cell suspension, bone marrow or a cell culture established from a patient's sample, or the culture supernatant or a xenograft established from a patient's tumor.

In another aspect, described herein is a method of detecting cancer in a subject, comprising, obtaining blood from the subject, contacting the blood with lectin-coated magnetic beads, isolation of the magnetic beads captured cells with a microfluidic magnetic separation device and assaying captured cells for CTC markers for e.g., GlcNAc, EpCAM, EphB4, HER2, EGFR, MUC-1, or a combination thereof.

In another aspect, described herein is a method for monitoring or assessing the effectiveness of a cancer treatment in a patient, comprising: (a) obtaining a first sample of the patient prior to the cancer treatment and establishing a baseline CTC count by isolating CTC using the method described above and enumerating a CTC count, wherein CTC count is defined as the amount of GlcNAc+ cells in the blood sample; (b) obtaining a second sample of the patient after the cancer treatment and determining a post-treatment level of CTC count by isolating CTC from the sample using the method described above and enumerating a CTC count; and (c) comparing the levels of post-treatment CTC count to the baseline CTC count, and optionally obtaining additional samples at different time intervals after the cancer treatment to determine a time-series for post-treatment CTC counts, wherein if the post-treatment CTC counts show a decreasing trend, the treatment is said to be effective, whereas if the post-treatment CTC count shows an increasing trend or stays at about the baseline level, the treatment is said to be ineffective. In some embodiments the method further comprises conducting cellular or molecular analysis on the isolated CTCs, wherein the cellular or molecular analysis is selected from immunochemical analysis, morphological analysis, genomics analysis, epigenomics analysis, transcriptomics analysis, proteomics analysis, DNA mutation analysis, whole genome analysis, protein and/or RNA expression level of a specific gene or a combination thereof.

In another aspect, described herein is a method for determining a prognosis of a patient suffering from cancer comprising:(a) obtaining a blood sample from the patient; (b) isolating CTCs from the blood sample by applying the method described above to the blood sample; (c) enumerating isolated CTC count, wherein CTCs are defined as the cells that are positive for GlcNAc expression; (d) determining a prognosis for the patient based on the CTC count.

In another aspect, described herein is a method for early detection of metastatic tumor in a patient, comprising: (a) obtaining a blood sample from the patient; (b) isolating CTCs from the blood sample by applying the method described above to the blood sample; (c) enumerating isolated CTC count, wherein CTC is defined as mannan-expressing cells; and (d) determining a diagnosis based on the CTC count, wherein if the CTC count is above a predetermined level, a likelihood of metastatic tumor is indicated.

In another aspect, described herein is a kit for isolating and enriching CTCs in a blood sample, comprising: a red blood cell (RBC) lysis reagent; a lectin-coated magnetic nanobeads; a cell culture or a nutrition medium; and an instruction insert having encoded thereon a human readable description of the methods embodied in the foregoing aspect. In some embodiments, the kit further comprises a separation column, wherein said column comprising: a body with an entry end and an exit end each having an opening disposed thereon; and a cylindrical hollow space connecting the openings at the entry end and the exit end to form a passage channel, wherein said column is pre-packaged with a plurality of spherical separation beads disposed in the passage channel, said separation beads are comprised of a ferromagnetic material coated with an anti-corrosion, and are capable of being magnetized to capture a cell labeled with lectin coated magnetic nanoparticles. In some embodiments, the kit further comprises fluorescent staining reagents and antibodies for cancer cell markers.

In another aspect, described herein is a composition comprising a CTC bound to a lectin molecule, further comprising the lectin molecule attached to a surface e.g. magnetic bead.

In another aspect, described herein is a method for generating cancer vaccine, comprising: (a) contacting a sample containing CTCs from a cancer patient with lectin molecule attached to surface; (b) isolating the captured CTCs; (c) combining the isolated CTCs or a component thereof with an adjuvant to generate a CTC-immunogen and (d) administering the CTC-immunogen to a subject, thereby producing a cancer vaccine.

In another aspect, described herein is a method for generating a patient-specific cancer vaccine, comprising: (a) contacting a sample containing CTCs from a patient with lectin molecule attached to surface; (b) isolating the captured CTCs; (c)

combining the isolated CTCs or a component thereof with a scaffold to generate a CTC-immunogen and (d) administering the CTC-immunogen to the patient, thereby producing a patient-specific cancer vaccine.

In some embodiments, CTCs in the cancer vaccine can be heat killed, inactivated, neutralized, chemically fixed, lyophilized to generate a CTC-immunogen prior to administering the CTC-immunogen to the patient, thereby producing a patient-specific cancer vaccine. In some embodiments, the scaffold comprises a biomaterial. The scaffold biomaterial can be selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-caprolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfite, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In some embodiments, the biomaterial is selected from the group consisting of poly(L-lactide-co-glycolide) acid (PLGA), mesoporous silica, and cryogel IP, and combinations thereof. In some embodiments, the scaffold is capable of localizing to antigen-presenting cells (APCs) in the subject, and activating the APCs to produce high titer antibodies against the pathogen. In some embodiments, CTC-immunogen further comprises an adjuvant. In some embodiments, CTC-immunogen is implanted subcutaneously. In some embodiments, of the above noted aspect, the lectin molecule is a MBL at least comprising the CRD. In some embodiments, the lectin molecule comprises an antibody Fc domain (FcMBL). In some embodiments, the lectin molecule is attached to a magnetic surface.

In another aspect, described herein is a composition comprising a CRD region of a lectin linked to anticancer therapeutic molecule. In another aspect, described herein is a composition comprising an mRNA encoding a MD region of a lectin linked to anticancer therapeutic molecule.

In another aspect, described herein is a composition comprising a CRD region of a lectin linked to an imaging agent. In another aspect, described herein is a composition comprising an mRNA encoding a CRD region of a lectin linked to an imaging agent In another embodiment, described herein is a method of treating cancer, the method comprising administering to a subject, a composition of foregoing aspects comprising a therapeutic molecule.

In another embodiment, described herein is a method for visualization of cancer, the method comprising administering to a subject, a composition of foregoing aspects comprising an imaging agent.

BRIEF DESCRIPTION OF THE DRAWINGS

FIG. 8. Table showing the binding efficiency of cells from different cancer lines to FcMBL: A549, H727, H358, H1975, MCF7, 4T1 (mouse) and weak binding to normal MCF10a epithelial cells. Depletion experiments were performed by incubating cells with 1 μm FcMBL coated magnetic beads and then separating the beads in saline, whole blood, blood diluted 1:10 in saline, and blood lysed with RBC lysis buffer.

DETAILED DESCRIPTION

Figure 1:
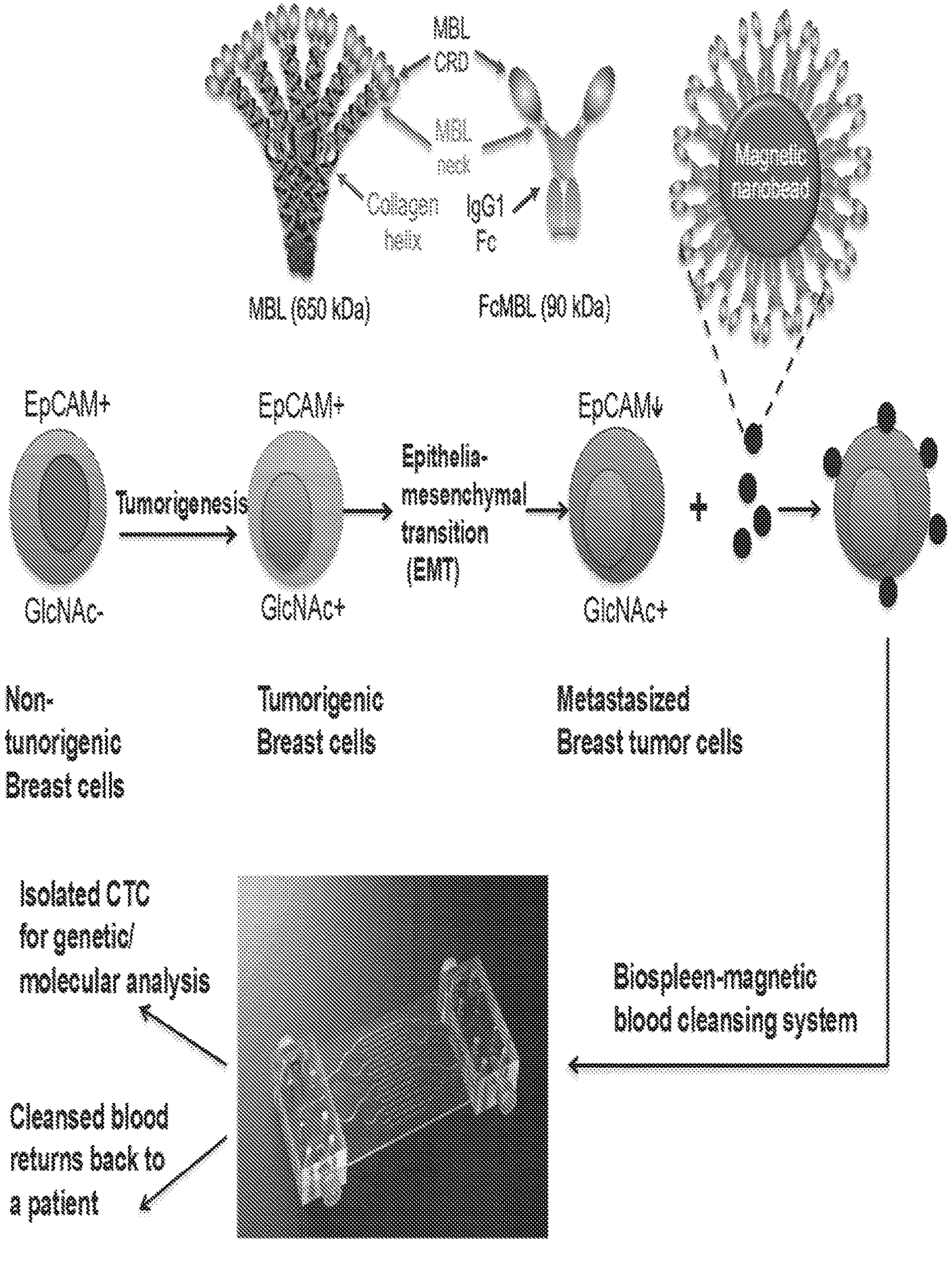
FIG. 1. FcMBL-coated magnetic particles capture metastasized tumor cells circulating in blood, which express N-acetylglucosamine (GlcNAc) on their surface while undergoing metastasis. FcMBL-magnetic beads selectively capture rare CTCs in blood and enable separation by the biospleen device. This will enable concentration of rare CTCs and deplete those cells responsible for cancer metastasis, reduce aggressiveness or likelihood of metastasis, and eventually improve outcome of cancer treatment.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Described herein are methods, compositions and kits for detection, capture and isolation of circulating tumor cells (CTCs) and applications thereof. It is contemplated that the methods, compositions and kits disclosed herein can be used to detect, capture and isolate cellular components of CTCs for example cell membrane and or secreted components of CTCs, for example extracellular vesicles, exosomes, microvesicles. In one aspect the present invention provides for use of carbohydrate binding proteins for example lectins, for detection, capture and isolation of cancer cells preferably CTCs. The term "lectin" as used herein refers to any molecules including proteins, natural or genetically modified (e.g., recombinant), that interact specifically with saccharides (e.g., carbohydrates) i.e. are carbohydrate binding proteins. Additional carbohydrate-binding proteins that can be included in the lectin molecule described herein can include, but is not limited to, lectins or agglutinins that are derived from a plant, e.g., Galanthus nivalis agglutinin (GNA) from the Galanthus (snowdrop) plant, and peanut lectin. In some embodiments, pentraxin family members, e.g., C-reactive protein can also be used as a carbohydrate-binding protein. Pentraxin family members can generally bind capsulated microbes. The carbohydrate-binding proteins can be wild-type, recombinant or a fusion protein.

The lectin molecule can comprise peptides, polypeptides, proteins, peptidomimetic or any structural mimics mimicking the carbohydrate binding region (e.g., Carbohydrate recognition domain (CRD or a fragment thereof), antibodies, antibody fragments (antigen-binding fragments of antibodies), carbohydrate binding proteins (e.g., lectins, glycoprotein, glycoprotein binding-molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof.

The lectins bind to carbohydrates with their carbohydrate recognition domain (CRD). In some embodiments, the lectin molecule comprises at least the CRD or a fragment thereof. In some embodiments, a lectin molecule can comprise a peptidomimetic that mimics any molecule or a fragment thereof that can specifically bind to the carbohydrate surface of a cancer cell or CTC, and/or secreted component thereof, for example extracellular vesicles, exosomes. For example, a lectin molecule can comprise a peptidomimetic that mimics any carbohydrate recognition domain or a fragment thereof, e.g., carbohydrate recognition domain of Mannose-binding lectin or a fragment thereof; or any carbohydrate recognition domain that is known in the art or a fragment thereof. In some embodiments, a lectin molecule comprises the full amino acid sequence of a carbohydrate-binding protein, a CRD or a fragment thereof. The CRD or a fragment thereof can be derived from a carbohydrate binding protein including but not limited to lectin, collectin, ficolin, mannose-binding lectin (MBL), maltose-binding protein, arabinose-binding protein, and glucose-binding protein. The respective carbohydrate recognition domains for such carbohydrate-binding proteins are known in the art, and can be modified for various embodiments of the lectin molecules described herein. A lectin molecule can be full length protein comprising a CRD, a fragment thereof comprising a CRD, a fragment of CRD. A lectin molecule can be wild-type, recombinant or a fusion molecule. In some embodiments, the lectin molecule can have an amino acid sequence of about 10 to about 300 amino acid residues, or about 50 to about 150 amino acid residues. In some embodiments, the carbohydrate binding domain can have an amino acid sequence of at least about 5, at least about 10, at least about 15, at least about 20, at least about 30, at least about 40, at least about 50, at least about 60, at least about 70, at least about 80, at least about 90, at least about 100 amino acid residues or more. For any known sequences of carbohydrate binding protein e.g. lectin and/or a carbohydrate recognition domain e.g. CRD or a mannose-binding lectin, one of skill in the art can determine the optimum length of amino acid sequence for the lectin molecule.

The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and Galanthus nivalis agglutinin (GNA) from the Galanthus (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the lectin molecule comprises at least of the CRD or a fragment thereof. In some embodiments, the lectin molecule is a C-type lectin or a carbohydrate recognition domain can be derived from a C-type lectin, or a fragment of a carbohydrate recognition domain derived from a C-type lectin. C-type lectin can include any carbohydrate-binding protein that requires calcium for binding. In some embodiments, the C-type lectin can include, but are not limited to, collectin, DC-SIGN, and CRD and/or fragments thereof.

Collectins are soluble pattern recognition receptors (PRRs) belonging to the superfamily of collagen containing C-type lectins. Exemplary collectins include, without limitations, mannose-binding lectin (MBL) (also known as mannan-binding lectin, mannan-binding protein, or mannose-binding protein), surfactant protein A (SP-A), surfactant protein D (SP-D), collectin liver 1 (CL-L1), collectin placental (CL-P1), conglutinin, collectin of 43 kDa (CL-43), collectin of 46 kDa (CL-46). In some embodiments of the present invention, the lectin molecule is a collectin, CRD thereof or a fragment derived from a CRD thereof.

Mannose-binding lectin (MBL), also known as mannose binding protein (MBP), or mannan-binding lectin or mannan-binding protein, is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and uptake of pathogens by tagging the surface of a pathogen to facilitate recognition and ingestion by phagocytes.

MBL is a member of the collectin family of proteins. A native MBL is a multimeric structure (e.g., about 650 kDa) composed of subunits, each of which contains three identical polypeptide chains. Each MBL polypeptide chain (containing 248 amino acid residues in length with a signal sequence: SEQ ID NO. 1) comprises a N-terminal cysteine rich region, a collagen-like region, a neck region, and a carbohydrate recognition domain (CRD). The sequence of each region has been identified and is well known in the art. SEQ ID NO. 2 shows a full-length amino acid sequence of MBL without a signal sequence.

The surface or carbohydrate recognition function of a native MBL is mediated by clusters of three C-type carbohydrate-recognition domains (CRDs) held together by coiled-coils of a-helices. The N-terminal portion collagen-like domain is composed of Gly-X-Y triplets. The short N-terminal domain contains several cysteine residues that form interchain disulfide bonds. Serum MBLs assemble into larger forms containing 2-4 trimeric subunits in rodents and as many as six subunits in humans. All three oligomeric forms of rat serum MBP, designated MBPA, can fix complement, although the larger oligomers have higher specific activity. Many species express a second form of MBP. In rats, the second form, MBP-C, is found in the liver. MBP-C does not form higher oligomers beyond the simple subunit that contains three polypeptides.

When a native MBL interacts with carbohydrates on the surface of microbes or pathogens, e.g., calcium-dependent binding to the carbohydrates mannose, N-acetylglucosamine, and/or fucose, it can form the pathogen recognition component of the lectin pathway of complement activation. The MBL binds to surface arrays containing repeated mannose or N-acetylglucosamine residues. It circulates as a complex with one or more MBP-associated serine proteases (MASPs) that autoactivate when the complex binds to an appropriate surface. The MBL and associated MASP proteins can activate C2/C4 convertase leading to the deposition of C4 on the pathogen surface and opsonization for phagocytosis. The native MBL can also activate coagulation function through MASP proteins.

In some embodiments, the lectin molecule is an engineered molecule that binds to CTCs, comprising at least one carbohydrate recognition domain or a fragment thereof, e.g., derived from MBL. In some embodiments, the engineered lectin molecule can comprises at least two, at least three or at least four carbohydrate recognition domains or a fragment thereof. In some embodiments, the engineered lectin molecules do not activate complement system or coagulation side effects that are present in a native lectin.

The full-length amino acid sequence of carbohydrate recognition domain (CRD) of MBL is shown in SEQ ID NO. 3. The carbohydrate recognition domain of an engineered MBL described herein can have an amino acid sequence of about 10 to about 300 amino acid residues, or about 50 to about 160 amino acid residues. In some embodiments, the CRD can have an amino acid sequence of at least about 5, at least about 10, at least about 15, at least about 20, at least about 30, at least about 40, at least about 50, at least about 60, at least about 70, at least about 80, at least about 90, at least about 100, at least about 150 amino acid residues or more. Accordingly, in some embodiments, the carbohydrate recognition domain of the engineered MBL molecule can comprise SEQ ID NO. 3. In some embodiments, the carbohydrate recognition domain of the engineered MBL molecule can comprise a fragment of SEQ ID NO. 3. Non-limiting examples of fragments are described in US 2014/0227723 A1, incorporated herein in its entirety. Modifications to such CRD fragments, e.g., by conservative substitution, are also within the scope described herein. In some embodiments, the MBL or a fragment thereof used in the lectin molecule described herein can be a wild-type molecule or a recombinant molecule.

As used herein, the terms “protein”, “peptide” and “polypeptide” are used interchangeably to designate a series of amino acid residues connected to each other by peptide bonds between the alpha-amino and carboxy groups of adjacent residues. The terms “protein”, “peptide” and “polypeptide” refer to a polymer of amino acids, including modified amino acids (e.g., phosphorylated, glycated, glycosylated, etc.) and amino acid analogs, regardless of its size or function. “Protein” and “polypeptide” are often used in reference to relatively large polypeptides, whereas the term “peptide” is often used in reference to small polypeptides, but usage of these terms in the art overlaps. The terms “protein”, “peptide” and “polypeptide” are used interchangeably herein when referring to a gene product and fragments thereof.

The exemplary sequences provided herein for the carbohydrate recognition domain of the lectin molecules are not construed to be limiting. For example, while the exemplary sequences provided herein are derived from a human species, amino acid sequences of the same carbohydrate recognition domain in other species such as mice, rats, porcine, bovine, feline, and canine are known in the art and within the scope described herein.

In some embodiments, the nucleic acid encodes a carbohydrate recognition domain having greater than 50% homology, including greater than 60%, greater than 70%, greater than 80%, greater than 90% homology or higher, to a fragment of at least 50, at least 60, at least 70, at least 80, at least 90, at least 100, at least 150 contiguous amino acids or more, of any known carbohydrate-binding molecules (e.g., mannose-binding lectins).

The term “carbohydrate recognition domain” as used herein refers to a region, at least a portion of which, can bind to carbohydrates on a surface of CTCs. In some embodiments, the carbohydrate recognition domain can comprise at least about 50% of its domain, including at least about 60%, at least about 70%, at least about 80%, at least about 90% or higher, capable of binding to carbohydrates on a CTC surface. In some embodiments, 100% of the carbohydrate recognition domain can be used to bind to CTCs.

In other embodiments, in addition to carbohydrate recognition domain, the lectin molecule can comprise additional regions that are not capable of carbohydrate binding, but can have other characteristics or perform other functions, e.g., to provide flexibility to the carbohydrate recognition domain when interacting with CTCs for example the neck region of MBL. A skilled artisan can readily modify the identified CRD and fragments thereof to modulate its orientation and binding performance to carbohydrates on a CTC surface, e.g., by theoretical modeling and/or in vitro carbohydrate-binding experiments.

In some embodiments, in addition to the carbohydrate recognition domain, the lectin molecule can further comprise a portion of a carbohydrate-binding protein. However, in some circumstances, complement or coagulation activation induced by a carbohydrate-binding protein or a fragment thereof can be undesirable depending on various applications, e.g., in vivo applications. In such embodiments, the portion of the carbohydrate-binding protein can exclude at least one of complement and coagulation activation regions. By way of example, when the carbohydrate-binding protein is mannose-binding lectin or a fragment thereof, the mannose-binding lectin or a fragment thereof can exclude at least one of the complement and coagulation activation regions located on the collagen-like region. In such embodiments, the mannose-binding lectin or a fragment thereof can exclude at least about one amino acid residue, including at least about two amino acid residues, at least about three amino acid residues, at least about four amino acid residues, at least about five amino acid residues, at least about six amino acid residues, at least about seven amino acid residues, at least about eight amino acid residues, at least about nine amino acid residues, at least about ten amino acid residues or more, around amino acid residue K55 or L56 of SEQ ID NO. 2.

Further regarding the carbohydrate recognition domain (CRD) or a fragment thereof, its binding characteristics can be manipulated by directed evolution for altered binding specificity. By way of example only, MBL can be modified so that it binds to a more limited set of sugars or other molecular features, with the result that the modified MBL will bind to CTCs of a specific type of cancer to provide a capability for cancer type identification.

The exemplary sequences provided herein for the carbohydrate recognition domain of the lectin are not construed to be limiting. For example, while the exemplary sequences provided herein are derived from a human species, amino acid sequences of the same carbohydrate recognition domain in other species such as mice, rats, porcine, bovine, feline, and canine are known in the art and within the scope described herein.

In some embodiments, the nucleic acid for example DNA or RNA encoding a carbohydrate recognition domain having greater than 50% homology, including greater than 60%, greater than 70%, greater than 80%, greater than 90% homology or higher, to a fragment of at least 50, at least 60, at least 70, at least 80, at least 90, at least 100, at least 150 contiguous amino acids or more, of any known carbohydrate-binding molecules (e.g., mannose-binding lectins).

The CRD domain is useful for the application at hand, and the other domains may be present or deleted depending on the needs of the user, and can be determined by routine testing. Modifications to CRD fragments, e.g., by conservative substitution, are also within the scope described herein.

In some embodiments the lectin molecule can comprise at least one CRD, including at least two, at least three, at least four, at least five, at least six, at least seven, at least eight, at least nine, at least ten or more CRD, can be linked together to form a multimeric carbohydrate recognition domain. A lectin molecule comprising multimeric CRD can have each of the individual CRD the same. Alternatively, a multimeric CRD can have at least one, at least two, or at least three CRD different from the rest. In such embodiments, CRD that share a common binding specificity for carbohydrates on a CTC surface can be used. By way of example only, the fibrinogen-like domain of several lectins has a similar function to the CRD of C-type lectins including MBL, and function as pattern-recognition receptors to discriminate pathogens from self. One of such lectins comprising the fibrinogen-like domain is serum violins. Serum violins have a common binding specificity for GlcNAc (N-acetylglucosamine), elastin or GalNAc (N-acetyl-galactosamine). The fibrinogen-like domain is responsible for the carbohydrate binding. In human serum, two types of ficolin, known as L-ficolin (also called P35, ficolin L, ficolin 2 or hucolin) and H-ficolin (also called Hakata antigen, ficolin 3 or thermolabile b2-macroglycoprotein), have been identified, and both of them have lectin activity. L-ficolin recognizes GlcNAc and H-ficolin recognizes GalNAc. Another ficolin known as M-ficolin (also called P3 5-related protein, ficolin 1 orficolinA) is not considered to be a serum protein and is found in leucocytes and in the lungs. L-ficolin and H-ficolin activate the lectin-complement path-way in association with MASPs. M-Ficolin, L-ficolin and H-ficolin has calcium-independent lectin activity. Accordingly, in some embodiments, a lectin molecule, can comprise MBL and L-ficolin carbohydrate recognition domains, MBL and H-ficolin carbohydrate recognition domains, or a combination thereof.

Any art-recognized recombinant carbohydrate-binding proteins or carbohydrate recognition domains can also be used in the lectin molecules. Non limiting examples of recombinant mannose-binding lectins, can be ones disclosed in the U.S. Pat. Nos. 5,270,199; 6,846,649; and U.S. Patent Application No. US 2004/0229212, the contents of which are incorporated herein by reference, can be used in constructing the lectin molecules described herein.

In other embodiments, the lectin molecule can comprise additional regions that are not capable of carbohydrate binding, but can have other characteristics or perform other functions, e.g., to provide flexibility to the carbohydrate recognition domain when interacting with CTCs. Accordingly in some embodiments, the lectin molecule is an engineered molecule comprising of a CRD of a carbohydrate binding protein preferably MBL, or a fragment of the CRD further attached to an linker for example, a Fc fragment. In some embodiments, the lectin molecule used in the methods and compositions disclosed herein, for example the CRD of the MBL, is further linked to Fc portion of an immunoglobulin, preferably IgG. In some embodiments, the lectin molecule is a genetically engineered version of MBL (FcMBL) as described in WO 2011/090954, US 2014/0227723 A1, US 2013/0035283 A1, WO 2013/012924 A2 the content of both of which is incorporated herein by reference.

Amino acid sequences for MBL and engineered MBL include, but are not limited to:

```
MBL full length
                                        (SEQ ID NO. 1)
MSLFPSLPLL LLSMVAASYS ETVTCEDAQK TCPAVIACSS

PGINGFPGKD GRDGTKGEKG EPGQGLRGLQ GPPGKLGPPG

NPGPSGSPGP KGQKGDPGKS PDGDSSLAAS ERKALQTEMA

RIKKWLTFSL GKQVGNKFFL TNGEIMTFEK VKALCVKFQA

SVATPRNAAE NGAIQNLIKE EAFLGITDEK TEGQFVDLTG

NRLTYTNWNE GEPNNAGSDE DCVLLLKNGQ WNDVPCSTSH

LAVCEFPI,

MBL without the signal sequence
                                        (SEQ ID NO. 2)
ETVTCEDAQK TCPAVIACSS PGINGFPGKD GRDGTKGEKG

EPGQGLRGLQ GPPGKLGPPG NPGPSGSPGP KGQKGDPGKS

PDGDSSLAAS ERKALQTEMA RIKKWLTFSL GKQVGNKFFL

TNGEIMTFEK VKALCVKFQA SVATPRNAAE NGAIQNLIKE

EAFLGITDEK TEGQFVDLTG NRLTYTNWNE GEPNNAGSDE

DCVLLLKNGQ WNDVPCSTSH LAVCEFPI
```

-continued

```
Carbohydrate recognition domain (CRD) of MBL
                                   (SEQ ID NO. 3)
VGNKFFLTNG EIMTFEKVKA LCVKFQASVA TPRNAAENGA

IQNLIKEEAF LGITDEKTEG QFVDLTGNRL TYTNWNEGEP

NNAGSDEDCV LLLKNGQWND VPCSTSHLAV CEFPI,
```

In some embodiments, the lectin molecule is attached to a surface for example, a solid surface. The surface can be made from a wide variety of materials and in a variety of formats. For example, in the form of beads (including polymer microbeads, magnetic microbeads, and the like), filters, fibers, screens, mesh, tubes, hollow fibers, porous scaffolds, plates, channels, other substrates commonly utilized in assay formats, and any combinations thereof. Examples of surfaces include, but are not limited to, nucleic acid scaffolds, protein scaffolds, lipid scaffolds, dendrimers, microparticles or microbeads, nanotubes, microtiter plates, medical apparatuses (e.g., needles or catheters) or implants, dipsticks or test strips, microchips, filtration devices or membranes, diagnostic strips, hollow-fiber reactors, microfluidic devices, living cells and biological tissues or organs, extracorporeal devices, mixing elements (e.g., spiral mixers). The surface can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

The format and/or material of the solid substrate depend on the application for example detection, in vivo targeting, capture, isolation of CTCs or a combination thereof. In some embodiments, the surface can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of polyimides, poly(ethylene glycol), polyvinyl alcohol, poly-ethyleneimine, and polyvinylamine, polyacrylates, polyamides, polyesters, polycarbonates, and polystyrenes, metals for e.g. titanium and stainless steel, or any biocompatible metal used in medical implants. In some embodiments, biocompatible materials can include paper substrate, e.g., as a substrate for a diagnostic strip. In some embodiments, biocompatible materials can include peptides or nucleic acid molecules, e.g., a nucleic acid scaffold such as a 2-D DNA sheet or 3-D DNA scaffold. Additional materials known in the art that can be used to coat the surface would be known to those skilled in the art and are thereby considered within the scope of the application. In some embodiments, the substrate surface can encompass an outer substrate surface and/or an inner substrate surface, e.g., with respect to a hollow structure. For example, a hollow fiber, hollow tube, the inner surface of a needle or catheter can be coated with the lectin molecules described herein, e.g., for removing any CTCs from a fluid before administering the fluid back to a subject. Devices that can be used for such applications are known in the art for example described by Kang, J H. et al. (2014), incorporated herein. Such devices can be easily adapted for the technology described herein. The lectin molecule can be coated onto the outer or inner surface of a hollow surface.

The amount of the lectin molecules attached, conjugated or coated on a surface can vary with a number of factors such as the area of the surface, conjugation/coating density, types/size of lectin molecules, and/or binding performance. A skilled artisan can determine the optimum density of lectin molecules on a surface using any methods known in the art. By way of example only, for magnetic microbeads including nanobeads) as a substrate (as discussed in detail later), the amount of the lectin molecules used for conjugating to or coating magnetic microbeads can vary from about 1 wt % to about 30 wt %, or from about 5 wt % to about 20 wt %. In some embodiments, the amount of the lectin molecules used for conjugating to or coating magnetic microbeads can be higher or lower, depending on a specific need.

The present invention provides for use of lectin molecule for detection, capture and isolation of cancer cells preferably CTCs.

The term "circulating tumor cells" or "CTCs" refers to tumor cells found in circulation of a patient having a tumor. This term typically does not include hematological tumors where the majority of the tumor is found in circulation. The term "cancer cells" and "tumor cells" are used interchangeably to refer to cells derived from a cancer or a tumor, or from a tumor cell line or a tumor cell culture. The term "cancer cells" and "tumor cells" and "circulating tumor cells" or "CTCs" can be used interchangeably. The term "metastatic cells" or "metastatic tumor cells" refers to the cells that have the ability to produce a metastasis or are already a part of a metastatic tumor. Accordingly, in some embodiments of the methods and compositions disclosed herein the CTCs are contacted with a lectin molecule. Lectin, for example MBL interact with carbohydrates e.g., mannose, N-acetylglucosamine and/or fucose. Accordingly, in some embodiments, the CTCs of some embodiments can express mannan carbohydrates, mannose, fucose and/or N-acetylglucosamine on their surface.

In some embodiments, the lectin molecule can be attached to a microparticle comprising at least one lectin molecule on its surface. The term "microparticle" as used herein refers to a particle having a particle size of about 0.001 μm to about 100 μm, about 0.005 μm to about 50 μm, about 0.01 μm to about 25 μm, about 0.05 μm to about 10 μm, or about 0.05 μm to about 5 μm. In one embodiment, the microparticle has a particle size of about 0.05 μm to about 1 μm. In one embodiment, the microparticle is about 0.09 μm—about 0.2 μm in size. It will be understood by one of ordinary skill in the art that microparticles usually exhibit a distribution of particle sizes around the indicated "size. "Unless otherwise stated, the term "size" as used herein refers to the mode of a size distribution of microparticles, i.e., the value that occurs most frequently in the size distribution. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy). The microparticles can be of any shape, e.g., a sphere. In general, any biocompatible material well known in the art for fabrication of microparticles can be used in embodiments of the microparticle described herein. Accordingly, a microparticle comprising a lipidic microparticle core is also within the scope described herein. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art.

Magnetic beads—In some embodiments, the lectin molecule is attached to a magnetic surface for e.g. magnetic beads, wherein the magnetic bead comprises on its surface at least one lectin molecule disclosed herein. Such lectin molecule attached magnetic microbeads can be used to separate CTCs from a test sample, e.g., but not limited to, any fluid, including a biological fluid such as blood. Attaching lectin molecules to a magnetic surface can be advantageous because the CTC bound magnetic surface can be easily separated from a sample fluid using a magnetic field gradient, be examined for the presence of CTCs, and/or be used to transfer the captured CTCs to conventional cellular and molecular assays. In some embodiments, the captured CTCs can be isolated from sample fluid by passing through a microfluidic magnetic separation device. Thus, in some embodiments, lectin molecule coated magnetic microbeads can be used to remove CTCs from any source or in any fluid, e.g., a biological fluid (e.g., blood sample). In some embodiments where the fluid is blood, after removal of the CTCs from the blood collected from a subject with the lectin molecule magnetic microbeads, the blood can be circulated back to the same subject as a therapeutic intervention. In some embodiments, the lectin molecule magnetic microbeads can be used in diagnostics as a means of collecting CTCs for identification of cancer type for e.g. in the form of liquid biopsy; Alternatively, the attachment surface can comprise a hollow-fiber reactor or any other blood filtration membrane or flow device (e.g., a simple dialysis tube, spiral mixer or static mixer) or other resins, fibers, or sheets to selective bind and sequester the CTCs. Such devices can be a component of a kit for detection, isolation and capture of CTCs from biological fluids e.g., blood.

The magnetic microbeads can be of any shape, including but not limited to spherical, rod, elliptical, cylindrical, and disc. As used interchangeably herein, the terms "magnetic microbeads" and "magnetic beads" can refer to a nano- or micro-scale particle that is attracted or repelled by a magnetic field gradient or has a non-zero magnetic susceptibility. The magnetic microbeads can be ferromagnetic, para-magnetic or super-paramagnetic. In some embodiments, magnetic microbeads can be super-paramagnetic. In some embodiments, magnetic microbeads can have a polymer shell for protecting the lectin molecule from exposure to iron provided that the polymer shell has no adverse effect on the magnetic property. For example, biocompatible polymer-coated magnetic microbeads can be used to remove CTCs from a test sample, e.g., a biological fluid, such as blood.

The magnetic microbeads can range in size from 1 nm to 1 mm. For example, magnetic microbeads can be about 2.5 nm to about 500 μm, or about 5 nm to about 250 μm in size. In some embodiments, magnetic microbeads can be about 5 nm to about 100 μm in size. In some embodiments, magnetic microbeads can be about 0.01 μm to about 10 μm in size. In some embodiments, magnetic microbeads can be about 0.05 μm to about 5 μm in size. In some embodiments, magnetic microbeads can be about 0.08 μm to about 1 μm in size. In one embodiment, magnetic microbeads can be about 10 nm to about 10 μm in size. In some embodiments, the magnetic microbeads can be magnetic nanobeads, e.g., with a size ranging from about 1 nm to about 1000 nm, from about 10 nm to about 500 nm, from about 25 nm to about 300 nm, from about 40 nm to about 250 nm, or from about 50 nm to about 200 nm. In one embodiment, the magnetic microbeads can be magnetic nanobeads with a size of about 50 nm to about 200 nm. Magnetic microbeads can be manipulated using magnetic field or magnetic field gradient. Such particles commonly consist of magnetic elements such as iron, nickel and cobalt and their oxide compounds. Magnetic microbeads are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232.; and No. 2007/0264199, the contents of which are incorporated herein by reference. Magnetic microbeads which can be functionalized with various functional groups, e.g., amino groups, carboxylic acid groups, epoxy groups, tosyl groups, or silica-like groups, are also widely and commercially available. Suitable magnetic microbeads are commercially available such as from AdemTech, Miltenyi, PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic microbeads that can be used herein can be any DYNA-BEADS® magnetic microbeads (Invitrogen Inc.), depending on the substrate surface chemistry.

Other surfaces: In some embodiments, the surface to which the lectin molecule can be attached can be living cells, or a biological tissue or organ. For example, the living cells can be associated with an immune response, and such cells include, but are not limited to, a phagocyte (macrophage, neutrophil, and dendritic cell), mast cell, eosinophil, basophil, and/or natural killer cell. Such compositions can be useful for e.g. in targeted cancer therapy.

In some embodiments, the bottom surface of a microtiter plate can be coated with the lectin molecule described herein, e.g., for detecting and/or determining the number of CTCs in a sample. After CTCs in the sample binding to the lectin molecules bound to the microwell surface, the rest of the sample can be removed. Detectable molecules that can also bind to CTCs (e.g., an lectin molecule conjugated to a detectable molecule as described herein, or antibodies to other CTC surface markers such as EpCAM conjugated to a detectable molecule) can then be added to the microwells with CTCs for detection of CTCs. Various signal detection methods for determining the amount of proteins, e.g., using enzyme-linked immunosorbent assay (ELISA), with different detectable molecules have been well established in the art, and those signal detection methods can also be employed herein to facilitate detection of the signal induced by CTC binding on the lectin molecules.

In some embodiments, the lectin molecules can be adapted for use in a dipstick and/or a test strip for detection and/or capture of CTCs. For example, a dipstick and/or a test strip can include at least one test area containing one or more lectin molecules described herein. In some embodiments, the lectin molecules can be conjugated or attached to a test area surface of the dipstick and/or a test strip. Methods for conjugating a protein to a substrate surface are known in the art, including, but not limited to direct cross-linking, indirect cross-linking via a coupling agent (e.g., a functional group, a peptide, a nucleic acid matrix such as DNA matrix), absorption, or any other art-recognized methods known in the art. The lectin molecule dipsticks and/or test strips described herein can be used as point-of-care diagnostic tools for CTC detection. By way of example only, a dipstick or test strip for CTC capture (e.g., made of membrane material such as nylon) can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. In some embodiments, the CTC-binding dipstick or test strip after contact with a test sample (e.g., a blood sample) can be further contacted with at least one additional agent to facilitate detection and/or capture of CTCs. For example, some embodiments of the dipstick or test strip after contact with a test sample (e.g., a blood sample) can be further contacted with a detectable label that is conjugated to a molecule that binds to a CTC component. Examples of such components can include, but are not limited to, one or more embodiments of the lectin molecule described herein, an antibody specific for the other known CTC surface markers e.g. EpCAM to be detected, a protein, a peptide, a carbohydrate or a nucleic acid that is recognized by the CTCs to be detected, and any combinations thereof.

The present invention discloses methods of isolation of CTCs using a lectin molecule from a biological fluid. As described herein, the lectin molecules attached to a surface, for example a magnetic surface can be used to detect, capture and isolate CTCs from a variety of samples, non-limiting examples of which include; body fluids such as whole blood plasma, plasma, any cell containing blood fraction, cerebrospinal fluid, joint fluid, urine, tears, feces, a fragmented tumor, a tumor cell suspension, a cell sample, cell culture established from a patients sample bone marrow (e.g., before transplantation), the culture supernatant or a xenograft established from a patients sample.

The lectin molecule attached to a surface, for example a magnetic surface can bind to a CTCs from a wide array of cancer types including but not limited to breast cancer, prostate cancer, colorectal cancer, lung cancer. Markers, or tumor-specific antigens can be used to confirm the identity of captured cells as tumor cells are well known in the tart and include, but are not limited to, binding agents to cell surface epitopes available from Miltengi Biotec GmbH.

As used herein, the terms "tumor-specific antigens" or "cancer antigens" or "cancer specific antigens" refer to a receptor polypeptide (e.g. a polypeptide that binds specifically to a molecule in the extracellular environment) that is present on the surface of a cancer cell and/or differentially expressed by cancer cells and can thereby be exploited in order to identify cancer cells. A tumor specific antigen can be a receptor displayed exclusively on cancer cells, a receptor displayed at a higher level on cancer cells than normal cells of the same or different tissue types, or a receptor displayed on both cancerous and normal cell types. In some embodiments, a tumor-specific can be a receptor that, in cancer cells, has altered (e.g. higher or lower than normal) expression and/or activity. In some embodiments, a tumor specific antigen can be a receptor that is implicated in the disease process of cancer. In some embodiments, a tumor specific antigen can be a receptor that is involved in the control of cell death and/or apoptosis. Some examples of cancer antigens include the cancer-testis (CT) antigens BAGE, GAGE, MAGE-1 and MAGE-3, NY-ESO-1, SSX. These antigens are found in melanoma, lymphoma, lung, bladder, colon, and breast carcinomas. Cancer antigens normally found in melanocytes, epithelial tissues, prostate, and colon also include the differentiation antigens Gp100, Melan-A/Mart-1, Tyrosinase, PSA, CEA, and Mammaglobin-A. These antigens are found in melanoma, prostate cancer, and in colon and breast carcinomas. Some cancer antigens are shared antigens that are ubiquitously expressed at low levels but overexpressed in cancers. Examples of overexpressed cancer antigens include p53, HER-2/neu, livin, and survivin, found in esophagus, liver, pancreas, colon, breast, ovary, bladder, and prostate carcinomas. Other cancer antigens are unique, such as β-catenin-m, β-Actin/4/m, Myosin/m, HSP70-2/m, and HLA-A2-R170J, which are associated with one or more of melanoma, non-small cell lung cancer, and renal cancer. Still other cancer antigens are the tumor-associated carbohydrate antigens that are normally found in epithelia tissues such as renal, intestinal, and colorectal tissues. These cancer antigens include GM2, GD2, GD3, MUC-1, sTn, abd globo-H, which can be found in melanoma, neuroblastoma, colorectal, lung, breast, ovarian, and prostate cancers. Additional tumor antigens, peptide epitopes, and descriptions thereof are described in U.S. Pat. Nos. 7,906,620; 7,910,692; 8.097,242; 7,935,531; 8,012,468; 8,097,256; 8,003,773; Tartour et al., Immunol Lett 2000; 74(1): 1-3, the contents of which are herein incorporated by reference in their entireties.

In an exemplary method for capture and/or detection of CTC in a test sample, the test sample is contacted with a lectin molecule attached to a surface for example a magnetic surface and CTC bound to lectin molecule are isolated using a microfluidic device, for example a magnetic microfluidic separation device. Use of a microfluidic device can automate the methods disclosed herein and/or allow analysis of multiple samples at the same time. One of skill in the art is well aware of methods in the art for collecting, handling and processing biological fluids which can be used in the practice of the present disclosure. The process described herein can allow sample analysis in short time periods. For example, the process can be completed in less than 6 hours, less than 5 hours, less than 4 hours, less than 3 hours, less than 2 hours, less than 1 hour, less than 30 minutes. In some embodiments, presence and identity of a CTC in the sample can be done within 10 minutes to 60 minutes of starting the process. The methods described herein can be utilized to detect the presence of CTCs in a sample of any given volume. In some embodiments, sample volume is about 0.25 ml to about 50 ml, about 0.5 ml to about 25 ml, about 1 ml to about 15 ml, about 2 ml to about 10 ml. In some embodiments, sample volume is about 5 ml. In one embodiment, sample volume is 8 ml. In some embodiments, prior to contacting with the lectin molecules, the sample can be preprocessed. The preprocessing can serve a number of purpose for example hemolyzing blood cells, dilution of samples, etc. A preprocessing agent can be present in the sample container or can be added to the sample in the container. When the sample is a biological fluid, the sample container can be a VACUTAINER®, e.g., a heparinized VACUTAINER®.

The preprocessing reagents include, but are not limited to, surfactants and detergents, salts, cell lysing reagents, anti-coagulants, degradative enzymes (e.g., proteases, lipases, nucleases, lipase, collagenase, cellulases, amylases and the like), and solvents, such as buffer solutions. In some embodiments, a preprocessing reagent is a surfactant or a detergent. In one embodiment, the preprocessing reagent is Triton X100. Amount of preprocessing reagent to be added can depend on a number of factors. Generally, the preprocessing reagent is added to a final concentration of about 0.1 mM to about 10 mM. If a liquid, the preprocessing reagent can be added so as to dilute the sample at least 10%, at least 20%, at least 30%, at least 40%, at least 50%, at least 60%, at least 60%, at least 80%, at least 90%, at least 1-fold, at least 2-fold, at least 3-fold, or at least 5-fold. One or more preprocessing agents can be a component of a kit to isolate and/or detect CTCs using the technology described herein. After preprocessing step, the sample is subjected to CTC capturing process, which can comprise mixing lectin molecules attached to a surface such as beads for e.g. lectin coated magnetic microbeads or lectin coated fluorescent microbeads. Amount of lectin molecule coated-microbeads added to the sample can be dependent on a number of different factors, such as, number of affinity molecules on each microbead, size of the microbead, binding affinity of the affinity molecule to the CTC, and concentration of the CTCs in the sample. Additionally, amount of coated-microbeads added to the sample can be adjusted to optimize the capture of CTCs. In some embodiments, amount of coated-microbeads added to the sample is such that a microbead binds with one CTC. However, each CTC can be bound to more than one coated-microbeads or conversely each microbead is bound to more than one CTC. In some embodiments, a plurality of coated-micro-beads can be contacted with a test sample. The plurality of coated-microbeads can comprise at least two subsets (e.g., 2, 3, 4, 5, or more subsets), wherein each subset of coated-microbeads have a pre-determined dimension. In some embodiments, the plurality of coated-microbeads can comprise a first subset of the coated-microbeads and a second subset of the coated-microbeads. In such embodiments, the first subset of the coated-microbeads each has a first predetermined dimension; and the second subset of the coated-microbeads each has a second predetermined dimension. The pre-determined dimension of a coated-micro-bead depends, in part, on the dimension of a microbead described herein to which the lectin molecules are conjugated. For example, the microbead can have a size of about 10 nm to 10 μm, about 20 nm to about 5 μm, about 40 nm to about 1 μm, about 50 nm to about 500 nm, or about 50 nm to about 200 nm. Additionally, each subset of the coated-microbeads can comprise on their surfaces substantially the same density or different densities of the affinity molecules (e.g., FcMBL or lectin molecules described herein).

Different subsets of the plurality of the coated-microbeads can be brought into contact with a test sample in any manner. For example, in some embodiments, the plurality of the coated-microbeads can be provided as a single mixture comprising at least two subsets of the coated-microbeads to be added into a test sample. In some embodiments, in order to distinguish among different subsets of the coated-microbeads, the coated-microbeads in each subset can have a distinct detection label, e.g., a distinctly-fluorescent label that can be sorted afterward, for example, by flow cytometry.

In other embodiments, the plurality of the coated-microbeads can be brought into contact with a test sample in a sequential manner. For example, a test sample can be contacted with a first subset of the coated-microbeads, followed by a contact with at least one more subsets of the coated-microbeads. The previous subset of the coated-microbeads can be removed from the test sample before addition of another subset of the coated-microbeads into the test sample. After addition of the lectin molecule coated-microbeads, they can be mixed in the sample to allow CTC to bind with the microbeads. This can be simply accomplished by agitating the sample, e.g., shaking or vortexing the sample and/or moving the sample around in a microfluidic device.

The volume of a test sample required for contacting the lectin molecule attached to a surface can vary with, e.g., the selection of the surface to which the lectin molecule is attached (e.g., microbeads, fibers, filters, filters, fibers, screens, mesh, tubes, hollow fibers), the concentration of CTCs present in a test sample, and/or the platform used to carry out the methods (e.g., a microfluidic device or a blood collection tube, a microtiter plate). In some embodiments, the test sample volume used to perform the assay described herein, e.g., in a microfluidic platform, can range from about 1 μL to about 500 μL, from about 5 μL to about 250 μL, or from about 10 μL to about 100 μL. In other embodiments, the test sample volume used to perform the assay described herein, e.g., in a tube platform, can range from about 0.05 mL to about 50 mL, from about 0.25 ml to about 50 ml, about 0.5 ml to about 25 ml, about 1 ml to about 15 ml, or about 2 ml to about 10 mi. In some embodiments, the test sample volume used to perform the assay described herein can be about 1 mL to about 5 mL. In one embodiment, the test sample volume used to perform methods described herein is about 5 ml to about 10 mL.

The sample mixture can be incubated for a period of time to allow the CTCs to bind onto the lectin molecule attached to a surface, e.g., incubation for at least one minute, at leak two minutes, at least three minutes, at least four minutes, at least five minutes, at least ten minutes, at least fifteen minutes, at least about twenty minutes, at least thirty minutes, at least forty-five minutes, or at least one hour. In one embodiment, the sample mixture can be incubated for a period of about 10-20 minutes. Such incubation can be performed at any appropriate temperature, In some embodiments, the incubation can be performed at a temperature ranging from about room temperature to about 37° C.

The captured CTCs bound to the lectin molecule are then subjected to an isolation process. The isolation can be carried out by passing the sample containing the CTCs bound to a lectin molecule through a microfluidic device. In some embodiments, where the lectin beads are bound to a magnetic surface, the separation can be carried out by using magnetic separation device for example microfluidic magnetic separation. Microfluidic devices including, those enabling magnetic separation are well known in the art US20130035630A1, CN202912946U, WO2010124227A3, US20070026469A1, US 2011/0039280, U.S. Pat. No. 6,365, 362. 13., Kang, J H. et al. (2014). In alternative embodiments, the lectin molecule is immobilized onto a microfluidic device and the sample is passed through the device for obtaining, sample free of CTCs. In some embodiments, the CTC-bound lectin molecule after isolated from the test sample or processing buffer can be washed with a buffer (e.g., TBST) to remove any residues of test sample, solution comprising the chelating agent or any unbound CTCs. The number of wash steps can range from 1 to many, e.g., 1, 2, 3, 4, 5, 6, 7, 8, 9, 10 or more wash steps. In one embodiments, the CTC bound to a lectin molecule after isolated from the solution comprising the chelating agent e.g. EDTA and/or the test sample can be washed with a buffer (e.g., TBST) for about at least 1-3 times.

In some embodiments, the release can be accomplished either by cleaving the bond tethering the lectin molecule to the solid surface, or by displacing the captured cells from the lectin molecule.

In one embodiment, the method of the invention utilizes cleavable bi-functional linkers for the capturing lectin molecule, e.g., photo-cleavable or chemical groups contained within the bi-functional linkers to enable release of the captured cells. Several photo-cleavable linkers are available to one skilled in the art, see, e.g. Kan oh, N., et al. (2010) Cleavable linker for photo-cross-linked small-molecule affinity matrix, Bioconjug. Chem. 21:182-186 and references cited therein. These bi-functional linkers can consist of different lengths and composition, such as single-stranded oligonucleotides that contain the photo-cleavable residue or an abasic site that can be cleaved enzymatically.

In another embodiment, the invention utilizes an avidin compound, e.g., avidin, streptavidin, nitroavidin or neutravidin, interacting with a biotinylated capturing lectin molecule to enable capture and release of cells. The avidin compound dissociates from the biotin part of the biotinylated antibody upon a change in pH of the solution from neutral to alkaline in the case of nitroavidin. The advantage of this embodiment is the ability to regenerate the binding surface.

In yet another embodiment, where cells are captured using peptide inhibitors, ligands or other binding partners to enable release of captured cells, the cells are made to dissociate from the matrix by adding excess of the binding agent in soluble form.

The captured CTC can remain bound on the lectin molecule during detection and/or analysis, or be isolated from it prior to detection and/or analysis. In some embodiments, a composition comprising a peptide comprising the CRD region of a lectin is linked to a detectable label for example an "imaging agent" or a "contrast agent". As used herein, the term "detectable label" refers to a agent capable of producing a detectable signal indicative of the presence of a target for example a cancer cells, CTCs, solid tumor, metastatic tumor. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and compositions described herein.

As used herein, the term "imaging agent" refers to an element or functional group in a molecule that allows for the detection, imaging, and/or monitoring of the presence and/or progression of a condition(s), pathological disorder(s), and/or disease(s) for example cancer. The imaging agent can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like. In some embodiments, the detectable labels also encompass any imaging agent (e.g., but not limited to, a bubble, a liposome, a sphere, a contrast agent, or any detectable label described herein) that can facilitate imaging or visualization of a tissue or an organ in a subject, e.g., for detection of CTCs and/or for diagnosis of cancer.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™.

Suitable radioisotopes include, but are not limited to, 99mTc, 95Tc, 111In, 62Cu, 64Cu, Ga, 68Ga, and 153Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to the lectin molecule. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to molecules such as the lectin molecules coated surfaces and carrier scaffolds disclosed herein.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. Exemplary methods for in vivo detection or imaging of detectable labels include, but are not limited to, radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), and computed Tomography (CT) or Computed Axial Tomography (CAT scan).

In some embodiments, the detectable label can include an enzyme. Exemplary enzymes for use as detectable labels include, but are not limited to, horseradish peroxidase (HRP), alkaline phosphatase (AP), or any combinations thereof. In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the CTCs isolated from or remained bound on the lectin molecule can be stained with at least one stain, e.g., at least one fluorescent staining reagent comprising a CTC-binding molecule, wherein the CTC-binding molecule comprises a fluorophore or a quantum dot. Examples of fluorescent stains include, but are not limited to, any CTC-binding molecule (e.g., antibodies targeting known surface markers of CTC, cancer cell markers, EMT markers) or any cancer cell binding proteins or peptides or oligonucleotides) typically conjugated with a fluorophore or quantum dot, and any fluorescent stains used for detection as described herein. In some embodiments, the detectable label is a gold particle. In some embodiments, the labeling molecule can comprise MBL or a lectin binding molecule described herein. In one embodiment, the labeling molecule comprises FcMBL. Without wishing to be bound by a theory, labeling molecules based on MBL, and FcMBL in particular, attach selectively to a broad range of CTCs, and so they enable the methods described herein to detect the CTCs from a variety of samples from an array of cancer types with high sensitivity and specificity.

Any method known in the art for detecting the particular label can be used for detection. Exemplary methods include, but are not limited to, spectrometry, fluorometry, microscopy imaging, immunoassay, and the like. While the CTC capture step can specifically capture CTCs, it can be beneficial to use a labeling molecule that can enhance this specificity. If imaging, e.g., microscopic imaging, is to be used for detecting the label, the staining can be done either prior to or after the CTCs have been laid out for microscopic imaging. Additionally, imaging analysis can be performed via automated image acquisition and analysis. In some embodiments, the methods disclosed herein can be used to detect cancer cells by imaging biopsy sections and or detect in vivo by injecting the compositions disclosed herein into the subject.

For optical detection, including fluorescent detection, more than one stain or dye can be used to enhance the detection or identification of the cancer cell for example CTC. For example, a first dye or stain can be used that can bind with a cancer cell and/or CTC, and a second dye or strain can be used that can bind with all cells for e.g. a DNA satin such as DAPI. Colocalization of the two dyes then provides enhanced detection or identification of the cancer cells by reducing false positive detection.

In some embodiments, microscopic imaging can be used to detect signals from label on the labeling agent. Generally, the cancer cells and/or CTCs in the subsample are stained with a staining reagent and one or more images taken from which an artisan can easily count the number of cells present in a field of view. In particular embodiments, CTCs can be detected through use of one or more enzyme assays, e.g., enzyme-linked assay (ELISA). In some embodiments, enzyme assays can be configured such that an enzyme will catalyze a reaction involving an enzyme substrate that produces a fluorescent product. Enzymes and fluorescent enzyme substrates are known and are commercially available (e.g., Sigma-Aldrich, St. Louis, Mo.). In some embodiments, enzyme assays can be configured as binding assays that provide for detection of CTCs. For example, in some embodiments, a labeling molecule for e.g., FcMBL, lectin molecule can be conjugated with an enzyme for use in the enzyme assay. An enzyme substrate can then be introduced to the one or more immobilized enzymes such that the enzymes are able to catalyze a reaction involving the enzyme substrate to produce a detectable signal. Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like. In some embodiments, the enzyme is a horseradish peroxidase (HRP). In some embodiments, the enzyme is an alkaline peroxidase (AP). Methods of conducting an ELISA assay are well known to those skilled in the art.

In some embodiments, the isolated CTCs can be further cultured in an in vitro culture system. In some embodiments, the CTCs are subjected to immunochemical analysis. The "immunochemical analysis" can include for example immunostaining the captured CTCs with one or more CTC markers known in the art. Non-limiting examples of CTC and/or tumor specific markers (also referred to as "tumor specific antigens") useful in the embodiments disclosed herein include cytokeratin, prostate-specific antigen (PSA), prostate specific membrane antigen (PSMA), mucin-1 (MUC-1), human epidermal growth factor receptor 2-HER2), AFP (a-fetoprotein), N-cadherin, epithelial cell adhesion molecule (EpCAM), EphB4or carcinoembryonic antigen (CEA) or a combination thereof. analysis of these markers can be done using methods such as flowcytometry or Fluorescence in situ hybridization (FISH). Accordingly the isolated CTCs can also be used for downstream immunocytochemical analysis, RT-PCR, PCR, FISH, flowcytometry, or other types of image cytometry.

It should be noted that a number of different cell analysis platforms can be used to identify and enumerate the captured CTCs. Examples of such analytical platforms are Immunicon's CellSpotter® system, a magnetic cell immobilization and analysis system, using microscopic detection for manual observation of cells described in Example II, and the CellTracks system, an a more advanced automatic optical scanning system, described in U.S. Pat. Nos. 5,876,593; 5,985,153 and 6,136,182 respectively. All of the aforementioned U.S. Patent Applications are incorporated by reference herein as disclosing the respective apparatus and methods for manual or automated quantitative and qualitative cell analysis. A decrease in the number of circulating tumor cells is indicative of an improvement in patient status or efficacy of treatment, whereas an increase indicates a worsening of the disease. Such devices may be used to advantage in the diagnostic and monitoring kits of the present invention. Using methods described herein, a composition comprising CTC cell population can obtained. A composition comprising the CTC population can be used for downstream analysis, for example, physical, chemical (e.g., biochemical), and/or molecular analysis. Various techniques can be used to conduct these studies to analyze physical, chemical and/or molecular features (e.g., DNA, RNA, microRNA, DNA methylation, and protein) of the CTCs. Examples of the analysis include, but are not limited to cytomorphological analysis, genomics analysis, proteomics analysis, transcriptomics analysis, epigenomics analysis, and any combinations thereof. In some embodiments, the analysis is performed on a single CTC. In some embodiments, the analysis is performed on a substantially pure population of CTCs. As used herein, non-limiting examples of cellular analysis include counting the number of the CTCs, cytomorphological analysis of the CTCs, and other techniques available for studying cellular details of cells. In some embodiments, one or more molecular features of the CTCs are analyzed. Examples of the molecular features include, but are not limited to, nucleic acid composition, protein composition, DNA methylation profile, protein glycosylation, and phosphorylation pattern. In some embodiments, nucleic acids (e.g., DNAs and RNAs) of the CTCs are isolated and analyzed. In some embodiments, whole genome amplification is performed before the molecular analysis. In some embodiments, the DNA sequence in cancer mutation hotspots in the CTCs is determined. Non-limiting examples of cancer mutation hotspots include mutation hotspots in genes such as Ras, p53, Braf, Pten, Egfr, Erccl, Rrml, Elm4, Alk, and Her2 gene. In some embodiments, the CTCs are analyzed for the presence or absence of gene amplification or translocation. For example, the CTCs can be analyzed to determine the presence or absence of Elm4-Alk translocation. Examples of methods that can be used for downstream analyses to characterize and/or analyze the cells include, but are not limited to, biochemical analysis; immunochemical analysis; image analysis; cytomorphological analysis; molecule analysis such as PCR, sequencing, determination of DNA methylation; proteomics analysis such as determination of protein glycosylation and/or phosphorylation pattern; genomics analysis; epigenomics analysis; transcriptomics analysis; and any combination thereof. In some embodiments, molecular features of the CTCs are analyzed by image analysis, PCR (including the standard and all variants of PCR), microarray (including, but not limited to DNA microarray, MMchips for microRNA, protein microarray, cellular microarray, antibody microarray, and carbohydrate array), sequencing, biomarker detection, or methods for determining DNA methylation or protein glycosylation pattern.

In some embodiments, the methods allow obtaining CTCs without significant disruption of the cells. Therefore, these methods allow preservation of cytologic details of the cells and detailed downstream analysis of the CTCs. Any suitable methods known in the art can be used to determine the structural integrity of the rare cells. Non-limiting examples of such methods include immunocytochemical procedures, fluorescence in situ hybridization (FISH), flow cytometry, image cytometry, and any combinations thereof. The methods disclosed herein allow studying the distribution of the markers of interest for example Epithelial to mesenchymal transition markers (EMT) (for example, mutation, gene expression, protein, DNA methylation, regulatory RNA (e.g., miRNA and siRNA), and etc.) among the CTCs.

Genomics, epigenomics, transcriptomics, and proteomics analysis of CTCs obtained by the methods described herein will provide a real-time window into the biology of a tumor and facilitate an understanding of tumor biology in real-time. For example, the condition of a cancer patient can be evaluated by analyzing sequence information obtained from a CTC. The sequence information can include insertion/deletion/mutation of the genomic sequence, methylation pattern of the DNA, and epigenetic characteristic of the DNA. In some embodiments, the condition of a cancer patient can be evaluated by analyzing biochemistry information obtained from a CTC. The biochemistry information can include information regarding protein glycosylation, protein phosphorylation and other post-translational modification on proteins.

In some embodiments, one or more gene mutations in the CTCs are determined. The types of gene mutation are not particularly limited. Non-limiting examples of gene mutation include insertions, deletions, substitutions, translocations, gene amplifications, and any combinations thereof. In some embodiments, the gene mutation is located in KRAS, BRAF, PTEN, EGFR, ERCC1, RRM1, ELM4, HER2, or ALK gene. In some embodiments, the DNA mutation is an EML4-ALK fusion or a gene amplification in Her2. In some embodiments, whole-genome analysis of the CTCs is performed.

In some embodiments, protein expression level of a cancer specific gene of the CTCs is determined. In some embodiments, RNA expression level of a cancer specific gene of the CTCs is determined. Examples of cancer specific gene include, but are not limited to, cytokeratin, prostate-specific antigen (PSA), prostate specific membrane antigen (PSMA), mucin-1 (MUC-1), human epidermal growth factor receptor 2 (HER2), AFP (a-fetoprotein), N-cadherin, epithelial cell adhesion molecule (EpCAM), epidermal growth factor receptor (EGFR), ERCC1, androgen receptor (AR), human equilibrative nucleoside transporter 1 (hENT1), RRM1, and carcinoembryonic antigen (CEA). Other non-limiting examples of the cancer specific gene include epithelial mesenchymal transition (EMT) markers are cancer stem cell (CSC) markers. Non-limiting examples of EMT markers include N-cadherin, vimentin, B-catenin (nuclear localized), Snail-1, Snail-2 (Slug), Twist, EF1/ZEB1, SIP1/ZEB2, and E47. Examples of CSC markers include, but are not limited to, CD 133 and CD44.

The embodiments disclosed herein also include methods for assessing or predict response of a patient suffering from cancer to a treatment, where the methods include providing a circulating tumor cell (CTC) or a substantially pure population of CTCs from the patient and performing one or more cellular or molecular analyses on the CTCs to determine treatment response in the patient. For example, expression levels of HER2 protein was found to correlate significantly with patients' response to anti-cancer drug lapatinib. Single CTCs obtained from a cancer patient using the methods disclosed herein can be analyzed for HER2 protein expression, and the HER2 protein expression level can be used to predict or assess the patient's response to lapatinib treatment and thus can be used in the development of an appropriate treatment regimen. As another example, the presence of cancer stem cell markers such as ALDH, CD44, CD 133, and CD 166 correlates with poor prognosis for colorectal cancer patients. However, certain therapies, i.e., dasatinib and curcumin combination therapy, has been shown to significantly reduce the number of cancer stem cells. Accordingly, the isolation and analysis of CTCs for cancer stem cell markers can be used to determine whether it is appropriate to treat a patient with certain chemotherapeutics. As such, methods disclosed herein for isolating single CTCs can be used to develop targeted therapies for cancer patients. As another example, molecular features (e.g., sequence and biochemistry information) obtained from the CTCs can be used to evaluate the patient's response to a cancer treatment, patient prognosis, patient diagnosis, or remission state of a patient.

The results obtained from the physical, chemical, and molecular analysis of CTCs can provide valuable information for various applications including, but not limited to, evaluating condition of the cancer patient, assessing or predicting cancer progression, assessing or predicting treatment response of the cancer patient, cancer prognosis, screening targets for cancer drugs, predicting treatment outcome, discovering novel biomarkers, and understanding response of cancer cell to therapeutic pressure.

The methods and compositions disclosed herein can be useful for cancer diagnosis and therapeutics. In some embodiments, the invention relates to a method of assessing a risk of developing a metastatic tumor in the patient. In some embodiments, the patient is carrying a tumor or had tumor a tumor. The patients sample can comprise whole blood, body fluid, any cell-containing blood fraction, a fragmented tumor, a tumor cell suspension, or a cell culture established from a patient's sample, or the culture supernatant or a xenograft established from a patient's tumor. In variations of this embodiment, the method further comprises a step of detecting one or more of the following biomarkers: EpCAM, CD146, CK5, CK7, CK18, CK19, CD44, Cd44v6, EphB4, IGF-1R, BCL2, HER2, HER3, CA19-9, CEA, CD133, MUC1, N-cadherin, Survivin, EGFR, KRAS, BRAF, p53, Pi3KCA, PTEN, KRT19, CD34, CD24, ACT2, VIM, NANOG, CXCR4 and TWIST1 in the captured cells. Other cancer epitopes (also referred to as "tumor specific antigens") are known in one art (and mentioned above) and can be used alone or in combination with the above-noted markers. In variations of this embodiment, the method further comprises analysis of the isolated CTCs using one or more of cellular and/or molecular methods described above.

In another embodiment, the invention is a method of detecting the presence of a malignant tumor or assessing metastatic potential of an existing or excised tumor in a patient by detecting mannan carbohydrates expressing CTCs in a patients sample. The sample may comprise whole blood, body fluid, any cell-containing blood fraction, a fragmented tumor, a tumor cell suspension, or a cell culture established from a patient's sample, or the culture supernatant. In this embodiment, the captured cells may be further characterized as CTCs and assessed for their numbers and gene expression profile comprising e.g. one or more of the biomarkers, for example ACT2, IGF-1R, BCL2, HER2, EphB4, CA19-9, CEA, CD24, CD44, CD133, CD146, CXCR4, TWIST1, VIM, NANOG, KRT19, MUC1, Survivin, EGFR, KRAS, BRAF, p53, Pi3KCA and PTEN. In variations of this embodiment, the method further comprises analysis of the isolated CTCs using one or more of cellular and/or molecular methods described above.

In yet another embodiment, the invention relates to a method of determining prognosis for a patient having a tumor, the method comprising determining the metastatic potential of the tumor by assessing the number of detected CTCs defined as mannan expressing cells within a patient sample e.g. blood, wherein the CTC count higher than that defined in the art for various cancer types is used as an indicator of poor outcome. The poor outcome can be for example in terms of progression free survival of the patient. According to the method, the prognosis may be formed for any malignant solid tumor known to have metastatic potential, including without limitation, lung cancer (e.g., non-small cell lung cancer (NSCLC), bone cancer, pancreatic cancer, cancer of the head or neck, melanoma, uterine cancer, ovarian cancer, cervical cancer, colorectal cancer, gastric cancer, breast cancer, endometrial cancer, thyroid cancer, prostate cancer, bladder cancer, kidney cancer (e.g., renal cell carcinoma), liver cancer (e.g., hepatocellular carcinoma), and cancers of the central nervous system (CNS), (e.g., glioma, glioblastoma multiforme or astrocytoma).

In some embodiments, the technology described herein relates to a method for assessing or monitoring the effectiveness of a cancer treatment for e.g. chemotherapy, radiation therapy, in a patient. When the level of CTC before a cancer treatment is compared to the level of CTC after the treatment, the comparison may serve as a benchmark to assess whether the particular treatment method is effective on the particular patient. Monitoring or assessment may be done by single point comparison or by taking a time-series of the CTC level and then analyzing the trend to make a diagnostic determination. In some embodiments of the method, the sample is collected from the patient prior to starting a therapeutic regimen, and at regular intervals post-treatment onset. In some embodiments of the method, the CTCs are captured and enumerated using the methods disclosed herein. The CTCs can be further analyses using one or more of the methods described above. The treatment is said to be effective if the number of captured CTCs are enumerated to be lower upon treatment onset and demonstrates a decreasing number in sample obtained at intervals after the onset. Accordingly, an increase in the number of captured CTCs in the sample obtained post-treatment onset and/or an increasing number in the samples obtained at regular intervals post-treatment onset indicates the treatment of choice is ineffective.

In some embodiments, the technology disclosed herein relates to a method for diagnosing metastatic tumor in a patient. The patient may be carrying a benign tumor or had been previously diagnosed with a benign tumor. The method encompasses capturing and enumerating the CTCs. A diagnosis of a metastatic tumor can be made based on a CTC count higher than a predetermined level.

In some embodiments, the binding of cancer cells and/or CTCs to the lectin molecule can facilitate detection and localization of cancer cells in a tissues and biological fluids of a subject. The binding further facilitates isolation and removal of cancer cells from a biological fluid of a subject, for e.g., blood. Accordingly, in one aspect the technology disclosed herein is a method of treatment of cancer. In some embodiments, the invention relates to a composition comprising, the lectin molecule attached to a surface linked to an imaging agent. The lectin molecule can be a CRD region of a lectin. The lectin molecule can be peptide of the lectin and/or the CRD region of the lectin or a nucleic acid for e.g. mRNA coding for the peptide of the lectin and/or the CRD region of the lectin. Thus in some embodiments, the compositions comprising the lectin molecule disclosed herein can detect and localize a tumor and/or tumor cells in a subject, which can then be removed by surgery or treated for example by targeted radiation therapy. In some embodiments, the surface substrate can be labeled for specific imaging of tumor sites. Non-limiting examples of radioisotopes tracers used for imaging e.g. in positron emission tomography include Carbon-11, Fluorine-18, Copper-64, Gallium-68, Bromine-76, Zirconium-89, Iodine-124. In some embodiments, the invention relates to a composition comprising, the lectin molecule attached to a surface linked to a therapeutic agent. The lectin molecule can be a CRD region of a lectin. The lectin molecule can be peptide of the lectin and/or the CRD region of the lectin or a nucleic acid for e.g. mRNA coding for the peptide of the lectin and/or the CRD region of the lectin. Thus, in these embodiments the compositions can be used to therapeutically target and treat a tumor in a subject. Non-limiting example of a therapeutic agents include Paclitaxel, Doxorubicin, Anastrozole, Everolimus, Melphalan, Rituximab, Bevacizumab, Trastuzumab, Imatinib. In some embodiments, the composition can further comprise at least one of an therapeutic agent and a drug delivery vehicle. As used herein, the term "drug delivery vehicle" generally refers to any material that can be used to carry an active agent to a target site. Examples of drug delivery vehicles includes, but are not limited to, a cell, a peptide particle, a polymeric particle, a dendrimer, a vesicle, a liposome, a hydrogel, a nucleic acid scaffold, an aptamer, and any combinations thereof. The term "therapeutic agent" as used herein refers to any entity with anti-cancer activity, i.e. the ability to inhibit or reduce the growth of a tumor and/or kill cancer cells, e.g., by at least about 30%, at least about 40%, at least about 50%, at least about 75%, at least about 90% or more, as compared to in the absence of an therapeutic agent. For therapeutic application, the compositions disclosed herein can be formulated or configured as per different applications using the methods known in the art.

In one aspect, the invention relates to methods for generating a cancer vaccine by capturing and isolating the CTCs from a sample. The method comprises of isolating the CTCs using a lectin molecule and combining the isolated CTCs or a component thereof for example cell membrane with a scaffold to generate a cancer vaccine composition. In some embodiments, the scaffold can comprise a biomaterial. Non limiting examples of a biomaterial are glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-caprolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, poly(L-lactide-co-glycolide) acid (PLGA), mesoporous silica, and cryogel IP, an adjuvant, and combinations thereof. In some embodiments, the scaffold composition can further comprise an adjuvant. In some embodiments, the composition, further comprises a factor that recruits cells of immune response for example dendritic cells, macrophages. Examples of factors that can recruit immune cells include but are not limited to cytokines, for e.g. GM-CSF. The scaffold can further comprise, of lectin molecules disclosed herein. In some embodiments, the lectin molecules comprise of the CRD region of a lectin. In some embodiments, the lectin molecule also comprises of the complement activation domain which can aid in activation of the complement cascade at the tumor site. In some embodiments, the cancer vaccine compositions are administered to a patient for e.g. subcutaneously to elicit an immune response in the patient. In some embodiments, the CTCs are isolated from a patient and then administered to the same patient in the form a patient specific cancer vaccine formulation. In some embodiments, the CTCs isolated using the lectin molecule can be preprocessed prior to administration to a subject. In some embodiments, the cells are subjected to radiation, are heat killed, lyophilized, subjected to physical degradation to separate its components, for example cell membrane, organelles Methods of preparation of cancer vaccine scaffolds are known in the art as shown in reference WO 2009/102465 A2, WO 2007/070660. The methods to determine the effectiveness of immune response can include imaging of tumor to detect a decrease in tumor size, Isolation and enumeration of CTCs in the blood post-administration of the vaccine. A decrease in cell numbers or a reduction of tumor size can indicate effective treatment. In one aspect, the technology described herein relates to a method to removing CTCs from blood using a process similar to apheresis. Exemplary method can comprise, a hollow fiber, hollow tube, the inner surface of a which can be coated with the lectin molecules described herein, e.g., for removing any CTCs from a fluid before administering the fluid back to a subject. Devices that can be used for such applications are known in the art for example described by Kang, J H. et al. (2014), incorporated herein. Such devices can be easily adapted for the technology described herein. The lectin molecule can be coated onto the outer or inner surface of a hollow surface.

As used herein, the term “administering,” refers to the placement of compositions disclosed herein, for e.g., in form of a cancer vaccine to elicit an cancer specific immune response in a patient or in form of a composition for therapeutically targeting cancer, detecting or localizing cancer or visualizing cancer as disclosed herein into a subject by a method or route that results in at least partial delivery of the composition at a desired site. Non limiting example of administration can be subcutaneous injection of the composition described herein.

The terms “increased”, “increase”, “increasing” or “enhance” are all used herein to generally mean an increase by a statically significant amount; for the avoidance of doubt, the terms “increased”, “increase”, or “enhance”, mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms, “decrease”, “reduce”, “reduction”, “lower” or “lowering,” or “inhibit” are all used herein generally to mean a decrease by a statistically significant amount. For example, “decrease”, “reduce”, “reduction”, or “inhibit” means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The term “adjuvant” as used herein refers to any agent or entity which increases the antigenic response or immune response by a cell to a cancer antigen. Examples of adjuvants include, but are not limited to mineral gels such as aluminum hydroxide; surface active substances such as lysolecithin, plutonic polyols, polyanions; other peptides; oil emulsions; and potentially useful human adjuvants such as BCG and *Corynebacterium parvum*. QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

In some embodiments, the composition as described herein further comprises an adjuvant. Adjuvants are a heterogeneous group of substances that enhance the immunological response against an antigen that is administered simultaneously. In some instances, adjuvants are added to a vaccine to improve the immune response so that less vaccine is needed. Adjuvants serve to bring the antigen—the substance that stimulates the specific protective immune response—into contact with the immune system and influence The type of immunity produced, as well as the quality of the immune response (magnitude or duration). Adjuvants can also decrease the toxicity of certain antigens; and provide solubility to some vaccine components.

In one embodiment, a vaccine composition as described herein further comprise an adjuvant. Examples of adjuvants include, but are not limited to QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

In some embodiments, suitable adjuvants include, but are not limited to, alum, MF59, LTR72 (a mutant of *E. coli* heat-labile enterotoxin with partial knockout of ADP-ribosyltransferase activity), polyphosphazene adjuvant, interleukins such as IL-1, IL-2, IL-4, IL-6, IL-8, IL-10 and IL-12, interferons such as alpha-interferon and gamma-interferon, tumor necrosis factor (TNF), platelet derived growth factor (PDGF), GCSF, granulocyte-macrophage colony-stimulating factor (GM-CSF), epidermal growth factor (EGF), and the like. Examples of adjuvants capable of stimulating cellular immune responses include cytokines secreted by helper T cells called Th1 cells, e.g., interleukin-2 (IL-2), interleukin-4, interleukin-12 (IL-12) and interleukin-18, fusion proteins having one of such Th1 type cytokines (e.g., IL-2) fused to the Fc portion of immunoglobulin G (IgG), interferons such as alpha-interferon, beta-interferon and gamma-interferon, and chemokines that attract T cells to infected tissues. Non-coding, ISS-enriched plasmid DNAs or ISS oligonucleotides (ISS-ODNs) can also be used in the present invention as adjuvants to enhance cellular immunity.

Using particulate systems as adjuvants, the antigens are associated or mixed with or into a matrix, which has the characteristics of being slowly biodegradable. Care must be taken to ensure that that the matrices do not form toxic metabolites. Preferably, the main kinds of matrices used are mainly substances originating from a body. These include lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are a critical element in all biological membranes.

Adjuvants for vaccines are well known in the art. Examples include, but not limited to, monoglycerides and fatty acids (e.g. a mixture of mono-olein, oleic acid, and soybean oil); mineral salts, e.g., aluminium hydroxide and aluminium or calcium phosphate gels; oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion); particulate adjuvants, e.g., virosomes (unilamellar liposomal vehicles incorporating influenza haemagluttinin), AS04 ([SBAS4] A1 salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array) and inert vehicles, such as gold particles. Adjuvants are further described in U.S. Pat. No. 6,890,540, U.S. Patent Application No. 2005/0244420, and PCT/SE97/01003, the contents of which are incorporated herein by reference in their entirety.

An aspect of the present invention is directed to a kit for capturing, detecting, isolating and/or enriching CTCs from a biological sample e.g. a blood sample. Kits in accordance with this aspect of the invention are designed to facilitate performance of the cell isolation method and CTC-based assays as described above. Thus, they generally include reagents required for performing the cell capture and isolation method and/or CTC enumeration step of the assays. They may also include containers, vials, and other tools for facilitating the manipulation of reagents and blood samples. Exemplary tools that may be included in the kit may include but are not limited to needles, blood collection vials, RBC lysis solution and reagent, depletion device and reagents (including but not limiting to separation beads, separation column, anti-CD45 depletion reagents, and nutrition medium in the presence of 1-20% FBS), enumeration reagents (including but not limiting to lectin molecule conjugated to detection label, anti-CD45 antibody, anti-EpCAM antibody, anti-PDPN antibody, anti-thyroid hormone receptor antibody, fluorescence-conjugated secondary antibodies, and DNA binding dye).

In some embodiments, the kit can comprise: (a) one or more containers containing a population of lectin molecules described herein; and (b) at least one reagent. In these embodiments, a user can generate their own composition of lectin molecule attached to a surface by conjugating the provided lectin molecules to their desired substrate, e.g., using any art-recognized conjugation chemistry and/or methods described herein. In such embodiments, the reagent can include, but is not limited to, a coupling agent for conjugation of lectin molecules to a surface. In some embodiments, the kit can further comprise one or more surface substrates (e.g., microbeads such as magnetic microbeads) to which the lectin molecules described herein are conjugated. In such embodiments, a user can further modify the surface chemistry of the provided substrate prior to conjugation of the lectin molecules to the substrate. In some embodiments, the kit can provide lectin molecules attached to a surface which are ready to use. Accordingly, in these embodiments, the kit can comprise: (a) one or more compositions of lectin molecules attached to a surface disclosed herein; and (b) at least one reagent. In some embodiments, the lectin molecule attached to a surface can include one or more CTC-binding dipsticks, e.g., as described herein. In other embodiments, the lectin molecule attached to a surface can include a population of CTC capturing microbeads (including, but not limited to, polymeric microbeads and magnetic microbeads). In some embodiments, the lectin molecule attached to a surface can include a population of magnetic microbeads coated with lectin molecules disclosed herein. The microbeads or magnetic microbeads can be provided in one or more separate containers, if desired. In some embodiments, the population of the microbeads or magnetic microbeads coated with lectin molecule contained in one or more containers can be lyophilized.

In some embodiments of any aspects of the kits described herein, the population of the microbeads or CTC-capturing microbeads can comprise at least one distinct subset of the microbeads For example, each distinct subset of the microbeads can be provided in a separate container. In some embodiments, the distinct subset of the microbeads can have a distinct size. In some embodiments, the distinct subset of microbeads can comprise on their surfaces a different density of lectin molecules from the rest of the population. In some embodiments, the distinct subset of lectin molecules coated microbeads, can comprise a different carbohydrate recognition domain from the others.

In some embodiments, the kit can comprise a separation column, for e.g., a cylindrical hollow space. The cylindrical hollow space can have an entry end for e.g., to inject the sample and an exit end, for example to remove the sample depleted of CTCs. The said column can be prepackaged with a plurality of separation beads, for example microbeads coated with one or more lectin molecules. The microbeads for example can comprise of ferromagnetic material coated with an anticorrosion (detailed above). The beads are capable of being magnetized to capture a cell labeled with lectin molecule attached to a magnetic head. In some embodiments, the kit further comprises fluorescent staining reagents and antibodies for cancer cell markers.

In some embodiments of any aspects of the kits described herein, the surface substrate (e.g., microbeads) or lectin molecule attached to a surface (e.g., lectin molecule coated microbeads) can further comprise a detection label. By way of example only, depending on the choice of detection methods, each distinct subset of the microbeads can comprise a unique detection label or the same detection label. For example, if each distinct subset of the lectin molecule coated microbeads is used in a different sampling well, the same detection label can be used on the lectin molecule coated microbeads. Detectable labels suitable for use in any kits provided herein include any composition detectable by spectroscopic, photochemical, biochemical, immunochemical, electrical, optical or chemical means. Any art-recognized detectable labels or the ones described herein can be included in the kits described herein. Means of detecting such labels are well known to those of skill in the art and exemplary detection methods are described herein. For example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments of any aspects described herein, the kits can further comprise one or more containers containing a population of detectable labels, wherein the detectable label is conjugated to a molecule. In some embodiments, at least one of the containers can contain a distinct population of detectable labels. The molecule conjugated to a detectable label can be any molecule that binds to a CTC. For example, in some embodiments, the molecule conjugated to a detectable label can comprise the same carbohydrate recognition domains as used in the lectin molecule coated microbeads (e.g., lectin molecule coated magnetic microbeads). In such embodiments, at least one population of the molecule-detectable label conjugate can comprise at least one carbohydrate recognition domain or a fragment thereof, e.g., derived from mannose-binding lectin or at least a portion of the CRD domain, e.g., encoded by SEQ ID NO. 3, or a fragment thereof. In some embodiments, the molecule conjugated to a detectable label can further comprise a Fc region of an immunoglobulin. In alternative embodiments, the molecule conjugated to a detectable label can comprise an antibody specific to an additional known marker of CTC for e.g., EpCAM, antibody specific to targets recognized by the lectin molecules described herein for e.g., N-Acetylglucosamine, or an antibody specific to at least one type of carbohydrate recognition domain (e.g., C-type lectins vs. S-type lectins) employed in the lectin molecules described herein. However, the antibody can also be a common antibody that binds to all cancer cells. Without limitations, a molecule attached to a detectable label can also include any ligand targeting microbial cell surface proteins or receptors, including carbohydrates, lipids, lectins, aptamers, protein, peptides, nucleic acid, polynucleotides, antibody or a portion thereof, an antibody-like molecule, peptidomimetic, and any combinations thereof.

Depending on the configuration/combination of the molecule-detectable label conjugates provided in the kit, different populations of the microbeads or magnetic microbeads can be mixed together with a test sample in a single reaction, or different populations each can be applied separately to different aliquots of the same test sample. After contacting the test sample with the lectin molecule coated microbeads or lectin molecule coated magnetic microbeads, any cancer cell and/or CTC recognized by the lectin molecules will bind to the microbeads or magnetic microbeads. In some embodiments where the kits comprise lectin molecule coated microbeads, the kits can further comprise a magnet adapted for use with the assay for isolation of the CTC bound to from a test sample. For example, if the assay is carried out in a blood collection tube, the magnet can be adapted for use with the blood collection tube, e.g., a magnet can be designed to be a magnet collar surrounding the blood collection tube to immobilize or isolate the CTC capturing magnetic microbeads from a test sample or an assay buffer. In any aspects of the kits provided herein, the kits can further comprise a portable readout machine or device, e.g., to determine and display the signal produced from the assay performed with the kit. For example, the readout machine or device can detect a colorimetric signal and/or a fluorescent signal produced from the assay of CTC detection performed with the kits described herein. In any aspects of the kits provided herein, when the detection label includes an enzyme (e.g., horseradish peroxidase, alkaline phosphatase and any others commonly used for colorimetric detection), the kits can further comprise one or more containers containing an enzyme substrate that produces a color change in the presence of the enzyme. One of skill in the art can readily recognize an appropriate enzyme substrate for any art-recognized enzymes used for colorimetric detection. By way of example only, an exemplary substrate for alkaline phosphatase can include BLIP/NOT or PAPP (p-Nitro phenyl Phosphate, Disodium Salt); an exemplary substrate for horseradish peroxidase can include TOMB.]. In any aspects of the kits provided herein, the kits can further comprise at least one microtiter plate, e.g., for performing the reaction and the detection. In some embodiments, the kits described herein can be used to screen a pharmaceutical product (e.g., a drug, a therapeutic agent, or an imaging agent), and/or a medical device (including, but not limited to, implantable devices) for the presence or absence of cancer cells.

Preferably, kits of the present invention will also include an instruction insert with instructions for performing the isolation method or assays as described above. The instruction insert may be in any human understandable format, including but not limited to a written booklet, an instructional DVD, an audio recording, and a printed link to an instructional website.

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. A subject can be male or female. Preferably, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with cancer A subject can be one who has been previously diagnosed with or identified as suffering from or under medical supervision for a cancer. The cancer can be metastatic or benign. A subject can be one who is diagnosed and currently being treated for, or seeking treatment, monitoring, adjustment or modification of an existing therapeutic treatment, or is at a risk of developing such a disorder. A subject can be one who has undergone chemotherapy or radiation therapy.

In some embodiments, the biological fluid sample for detection, capture and/or isolation of CTCs are from a patient suffering from cancer. In some embodiments, the biological fluid sample are from a subject suspected of cancer. In some embodiment, the cancer patient is receiving or has been treated with cancer treatment(s). In some embodiments, the CTCs are obtained from a blood sample. In some embodiments, the CTCs are from body fluid. The types of cancer for which the methods and compositions disclosed herein can be used for diagnosis and prognosis and therapeutics are not particularly limited. The cancer can be, for example, lung cancer, esophageal cancer, bladder cancer, gastric cancer, colon cancer, skin cancer, papillary thyroid carcinoma, colorectal cancer, breast cancer, lymphoma, pancreatic cancer, prostate cancer, ovarian cancer, pelvic cancer, and testicular cancer.

The terms “disease”, “disorder”, or “condition” are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term “in need thereof” when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

In accordance with the various embodiments, described herein, a test sample or sample, including any biological fluid, body fluid, which can be processed or preprocessed, that is suspected of comprising a cancer cell and/or CTC can be subjected to methods, assay, kits and system disclosed herein. The sample can be aqueous or non-aqueous. Non-limiting example of biological fluids include from a body fluid, such as whole blood, plasma, any cell-containing blood fraction, cerebrospinal fluid, joint fluid, urine, tears or feces. In some embodiments, the biological fluid sample obtained from a subject, e.g., a mammalian subject such as a human subject or a domestic pet such as a cat or dog, can contain cells from the subject. In other embodiments, the biological fluid sample can contain non-cellular biological material, such as non-cellular fractions of blood, saliva, or urine, which can be used to measure plasma/serum biomarker expression levels. The biological fluid sample can be freshly collected from a subject or a previously collected sample. In some embodiments, the biological fluid sample used in the assays and/or methods described herein can be collected from a subject no more than 24 hours, no more than 12 hours, no more than 6 hours, no more than 3 hours, no more than 2 hours, no more than 1 hour, no more than 30 mins or shorter. In some embodiments, the biological fluid sample or any fluid sample described herein can be treated with a chemical and/or biological reagent described herein prior to use with the assays and/or methods described herein. In some embodiments, at least one of the chemical and/or biological reagents can be present in the sample container before a fluid sample is added to the sample container. For example, blood can be collected into a blood collection tube such as VACUTAINER®, which has already contained heparin. Examples of the chemical and/or biological reagents can include, without limitations, surfactants and detergents, salts, cell lysing reagents, anticoagulants, degradative enzymes (e.g., pro-teases, lipases, nucleases, collagenases, cellulases, amylases), and solvents such as buffer solutions. In some embodiments, the sample can be a fragmented tumor, a tumor cell suspension, or a cell culture established from a patients sample, or the culture supernatant, or a xenograft established from a patients tumor or a tumor biopsy or tissue section comprising tumor.

Some embodiments of the technology described herein can be defined according to any of the following numbered paragraphs:

1. A method for capturing circulating tumor cells (CTCs) from biological fluids of a subject, comprising: contacting the biological fluid with a lectin molecule attached to a surface.
2. The method of paragraph 1, wherein the surface is a bead, hollow fiber, porous scaffold, particle, or well.
3. The method of paragraph 1, wherein the surface is magnetic.
4. The method of paragraph 1, further comprising isolation of the captured CTCs.
5. The method of paragraph 4, wherein the isolation comprises passing the biological fluid containing captured CTCs through a microfluidic magnetic separation device.
6. The method of paragraphs 1-5, wherein the CTCs express mannan carbohydrates on their cell surface.
7. The method of paragraphs 1-5, wherein the CTCs express carbohydrates containing D-mannose and L-fucose onto its cell surface.
8. The method of paragraphs 1-7, wherein the biological fluid is selected from a body fluid, such as whole blood, plasma, any cell-containing blood fraction, cerebrospinal fluid, bone marrow (e.g., before transplantation), cell sample (e.g., before transplantation), joint fluid, urine, tears or feces.
9. The method of paragraphs 1-8, wherein the lectin molecule contains a collectin carbohydrate recognition domain (CRD).
10. The method of paragraphs 1-9, wherein the lectin molecule is a Mannose binding lectin (MBL).
11. The method of paragraph 1, wherein the lectin molecule is a ficolin.
12. The method of paragraph 1, wherein the lectin molecule is a dectin.
13. The method of paragraph 1-10, wherein the lectin molecule is a C-type lectin.
14. The method of paragraph 1, wherein the lectin molecule is a fucose-binding lectin.
15. The method of paragraph 14, wherein the fucose-binding lectin is Hemopexin.
16. The method of paragraphs 1-15, wherein the lectin molecule comprises of carbohydrate recognition domain (CRD).
17. The method of paragraph 16, wherein the CRD is that of a mannose binding lectin.
18. The method of paragraph wherein the lectin is an S-type lectin.
19. The method of paragraph 18, wherein the S-type lectin is Galectin.

20. The method of paragraphs 1-19, wherein the lectin molecule is an engineered molecule.
21. The method of paragraphs 1-20, wherein the engineered molecule further comprises the Fc region of an immunoglobulin.
22. The method of paragraph 21, wherein the engineered molecule is FcMBL.
23. The method of paragraphs 1-22, wherein the lectin molecule is of mammalian origin.
24. The method of paragraph 23, wherein the lectin molecule is of human origin.
25. The method of paragraphs 1-24, wherein the lectin molecule comprises at least 80% amino acid sequence identity to human lectin and retains at least 80% of its biological ability.
26. A method of analyzing a CTC captured from a sample by the method of paragraphs 1-5, wherein the analysis comprises cell culture, an immunochemical analysis, morphological analysis, genomics analysis, metabolomics, epigenomics analysis, transcriptomics analysis, proteomics analysis, DNA mutation analysis, whole genome analysis, protein and/or RNA expression level of a specific gene or a combination thereof.
27. A method of paragraph 26, wherein the analysis is used to assess a risk of developing a metastatic tumor in a patient carrying or having carried a tumor.
28. The method of paragraph 26, wherein the sample comprises whole blood, body fluid, any cell-containing blood fraction, a fragmented tumor, biopsy, aspirate, a tumor cell suspension, or a cell culture established from a patient's sample, or the culture supernatant or a xenograft established from a patient's tumor.
29. A method of detecting cancer in a subject, comprising, obtaining a biological fluid or cell sample from the subject, contacting the sample with lectin-coated magnetic beads, isolation of the magnetic beads captured cells with a microfluidic magnetic separation device and assaying captured cells for CTC markers.
30. A method of paragraph 29, wherein the CTC markers are selected from GlcNAc, EpCAM, EphB4, HER2, EGFR, MUC-1, or a combination thereof.
31. A method for monitoring or assessing the effectiveness of a cancer treatment in a patient, comprising:
(a) obtaining a first sample of the patient prior to the cancer treatment and establishing a baseline CTC count by isolating CTC using the method of paragraphs 1-5 and enumerating a CTC count, wherein CTC count is defined as the number of cells in the blood sample expressing mannan on their surface;
(b) obtaining a second sample of the patient after the cancer treatment and determining a post-treatment level of CTC count by isolating CTC from the sample using the method of paragraphs 1-5 and enumerating a CTC count; and
(c) comparing the levels of post-treatment CTC count to the baseline CTC count, and optionally obtaining additional samples at different time intervals after the cancer treatment to determine a time-series for post-treatment CTC counts, wherein if the post-treatment CTC counts show a decreasing trend, the treatment is said to be effective, whereas if the post-treatment CTC count shows an increasing trend or stays at about the baseline level, the treatment is said to be ineffective.
32. The method of paragraph 31 further comprising conducting cellular or molecular analysis on the isolated CTCs, wherein the cellular or molecular analysis is selected from cell culture, immunochemical analysis, morphological analysis, genomics analysis, metabolic analysis, epigenomics analysis, transcriptomics analysis, proteomics analysis, DNA mutation analysis, whole genome analysis, protein and/or RNA expression level of a specific gene or a combination thereof.
33. A method for determining a prognosis of a patient suffering from cancer comprising:
(a) obtaining a blood sample from the patient;
(b) isolating CTCs from the blood sample by applying the method of paragraphs 1-5 to the blood sample;
(c) enumerating isolated CTC count, wherein CTCs are defined as the cells that are positive for mannan expression;
(d) determining a prognosis for the patient based on the CTC count.
34. A method for early detection of metastatic tumor in a patient, comprising:
(a) obtaining a blood sample from the patient;
(b) isolating CTCs from the blood sample by applying the method of paragraphs 1-5 to the blood sample;
(c) enumerating isolated CTC count, wherein CTC is defined as mannan-expressing cells; and
(d) determining a diagnosis based on the CTC count, wherein if the CTC count is above a predetermined level, a likelihood of metastatic tumor is indicated.
35. A kit for isolating and enriching CTCs in a blood sample, comprising:
a red blood cell (RBC) lysis reagent;
lectin-coated magnetic nanobeads;
cell culture or a nutrition medium; and
an instruction insert having encoded thereon a human readable description of the method of paragraphs 1-5.
36. The kit of paragraph 35, further comprising a separation column, wherein said column comprising:
a body with an entry end and an exit end each having an opening disposed thereon; and
a cylindrical hollow space connecting the openings at the entry end and the exit end to form a passage channel,
wherein said column is pre-packaged with a plurality of spherical separation beads disposed in the passage channel, said separation beads are comprised of a ferromagnetic material coated with an anti-corrosion, and are capable of being magnetized to capture a cell labeled with lectin coated magnetic nanoparticles.
37. The kit of paragraph 35-36, further comprising fluorescent staining reagents and antibodies for cancer cell markers.
38. A composition comprising a CTC bound to a lectin molecule.
39. The composition of paragraph 38, further comprising the lectin molecule attached to a surface, wherein the surface is magnetic bead.
40. A method for generating cancer vaccine, comprising:
(a) contacting a sample containing CTCs from a cancer patient with lectin molecule attached to surface;
(b) isolating the captured CTCs;
(c) combining the isolated CTCs or a component thereof with an adjuvant generate a CTC-immunogen and
(d) administering the CTC-immunogen to a subject, thereby producing a cancer vaccine.
41. A method for generating a patient-specific cancer vaccine, comprising:
(a) contacting a sample containing CTCs from a patient with lectin molecule attached to surface;
(b) isolating the captured CTCs;
(c) combining the isolated CTCs or a component thereof with an adjuvant to generate a CTC-immunogen and (d) administering the CTC-immunogen to the patient, thereby producing a patient-specific cancer vaccine.

42. A method for generating a patient-specific cancer vaccine, comprising:
   (a) contacting a sample containing CTCs from a patient with lectin molecule attached to surface;
   (b) isolating the captured CTCs;
      (c) combining the isolated CTCs or a component thereof with a scaffold to generate a CTC-immunogen and (d) administering the CTC-immunogen to the patient, thereby producing a patient-specific cancer vaccine.
43. The method of paragraphs 40-41, wherein the captured CTCs are heat killed, inactivated, neutralized, chemically fixed, lyophilized to generate a CTC-immunogen prior to step (d)
44. The method of paragraphs 42, wherein the scaffold comprises a biomaterial.
45. The method of paragraphs 44, wherein the biomaterial is selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-caprolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof.
46. The method of paragraph 44, wherein the biomaterial is selected from the group consisting of poly(L-lactide-co-glycolide) acid (PLGA), mesoporous silica, and cryogel IP, and combinations thereof.
47. The method of paragraphs 42-46, wherein the scaffold is capable of localizing to antigen-presenting cells (APCs) in the subject, and activating the APCs to produce high titer antibodies against the pathogen.
48. The method of paragraphs 42, wherein the CTC-immunogen further comprises an adjuvant.
49. The method of paragraphs 42, wherein the CTC-immunogen is implanted subcutaneously.
50. The method of paragraphs 42, wherein the lectin molecule is a MBL at least comprising the CRD.
51. The method of paragraphs 42, wherein the lectin molecule comprises an antibody Fc domain (FcMBL).
52. The method of paragraphs 42, wherein the lectin molecule is attached to a magnetic surface.
53. A composition comprising a CRD region of a lectin linked to an anticancer therapeutic molecule.
54. A composition comprising an mRNA encoding a CRD region of a lectin linked to anticancer therapeutic molecule.
55. A composition comprising a CRD region of a lectin linked to an imaging agent.
56. A composition comprising an mRNA encoding a CRD region of a lectin linked to an imaging agent.
57. A method of treating cancer, the method comprising, administering to a subject, the composition of paragraphs 53-56.
58. A method for visualization of cancer, the method comprising administering to a subject, the composition of paragraphs 53-56 and imaging cancer.
59. The method of paragraph 31 or 32, wherein the CTC is confirmed with a tumor-specific marker (e.g., GlcNAc or EpCam).

EXAMPLES

The following examples illustrate some embodiments and aspects of the invention. It will be apparent to those skilled in the relevant art that various modifications, additions, substitutions, and the like can be performed without altering the spirit or scope of the invention as defined in the claims which follow. The technology described herein is further illustrated by the following examples which is no way should be construed as being further limiting.

Example 1

Binding of FcMBL-Magnetic Beads to Tumorigenic Human Breast Cancer Cells

Figure 2:
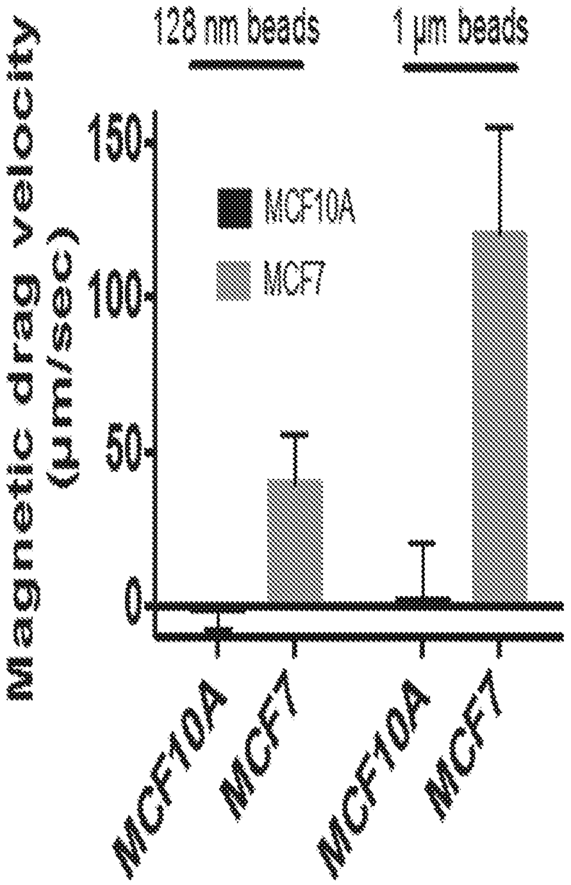
FIG. 2. The magnetic drag velocity of the human breast tumor cells labeled with FcMBL magnetic beads as measured in a microfluidic channel filled with saline. MCF7, human tumorigenic breast tumor cells, shows significantly high drag velocity, implying that FcMBL beads capture human breast tumor cells whereas non-tumorigenic human breast tissue cells do not interact with FcMBL beads.

Specific interaction of FcMBL only with tumorigenic human breast cancer cells (MCF7), not with non-tumorigenic breast cells (MCF10A) was validated. MCF7 and MCF10A cells ($10^4$ cells/1 mL) were incubated with 2.5 μg/ml of 128 nm (or 1 um) FcMBL coated magnetic nanoparticles blocked with PEG (polyethylene glycol)-biotin in TBS (Tries buffered saline) with 2 mM calcium for 20 min. The sample was flowed through the microfluidic channels disclosed in Kang, J H. et al. (2012), and the drag velocity was measured of the cells driven by the magnetic flux density gradients as described in Kang, J H. et al. (2012). The magnetic drag velocity of MCF7 was determined about 40 μm/sec and 120 μm/sec when they were bound to 128 nm and 1 um FcMBL magnetic beads, respectively, while those of MCF10A had −0.95 μm/sec and 2.3 μm/sec of magnetic drag velocity when they were incubated with FcMBL magnetic beads of 128 nm and 1 um sizes, respectively. (FIG. 2).

Example 2

Quantifying CTC-Isolation Efficiency Using Human Breast Tumor Cell Line

To determine the quantitative efficiency of cell isolation of the method, MCF7 cells (~$10^5$ cells in total) stained with calcein AM (green fluorescent when viable) and labeled with 1 um FcMBL magnetic beads were spiked either into 10 mL of buffer or pig whole blood. The sample was flowed through the biospleen device at each flow rate of 10 mL/h, 100 mL/h, 500 mL/h, 1 L/h, and 2 L/h, and then isolation efficiency was measured by counting the cell numbers from the inlet and the outlet. The spiked cells were quantitated in buffer and blood using disposable hemocytometers as described in Kang, J H. et al. (2012). The isolation efficiency of the 1 um FcMBL magnetic bead captured MCF7 cells was above 95% at flow rates from 10 mL/h~500 mL/h, and it decreased down to ~66% as the flow rates go up to 2.0 L/h.

Example 3

FcMBL Capturing CTCs in a Tumor Bearing Mice Model

Staining Breast Tumor Cells of Transgenic Mice with FcMBL

Figure 3:
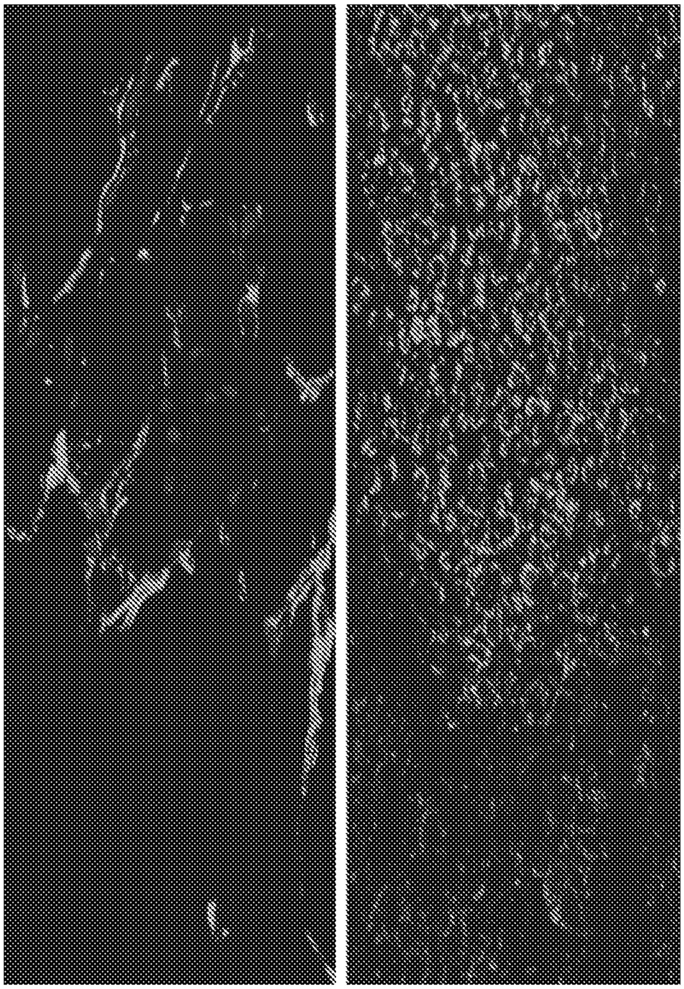
FIG. 3. Immunocytochemistry image of mammary ducts of 20 week old wild type mice (left) and 22 week old transgenic mice (right). Carbohydrates on tumorigenic epithelial cell surface were bound with FcMBL in the transgenic mice whereas in the wildtype mice (left) FcMBL bound to polysaccharide-rich glycosaminoglycan elements of ECM, not epithelial cells.

Preferential binding of FcMBL to tumor cells, compared to normal cells was examined, within tissues in vivo. Primary breast tumors that spontaneously developed in FIB C3(1)-SV40 T-antigen mammary tumor-bearing transgenic mice was used for these studies. Mammary tissue samples were surgically removed from 22 and 20 week old transgenic mice or wild type mice, and cryo-sectioned for immunohistochemistry (IHC) staining with fluorescently-labeled FcMBL. Epithelial tumor cells in mammary duct of transgenic mice (22 week) (blue: DAPI) bound FcMBL (green) strongly, whereas wild type epithelial cells did not show any evidence binding to FcMBL. Fibrillar fluorescence staining in the wild type mammary duct is most likely due to polysaccharide-rich glycosaminoglycan elements of the extracellular matrix (ECM) (FIG. 3).

Example 4

Figure 4:
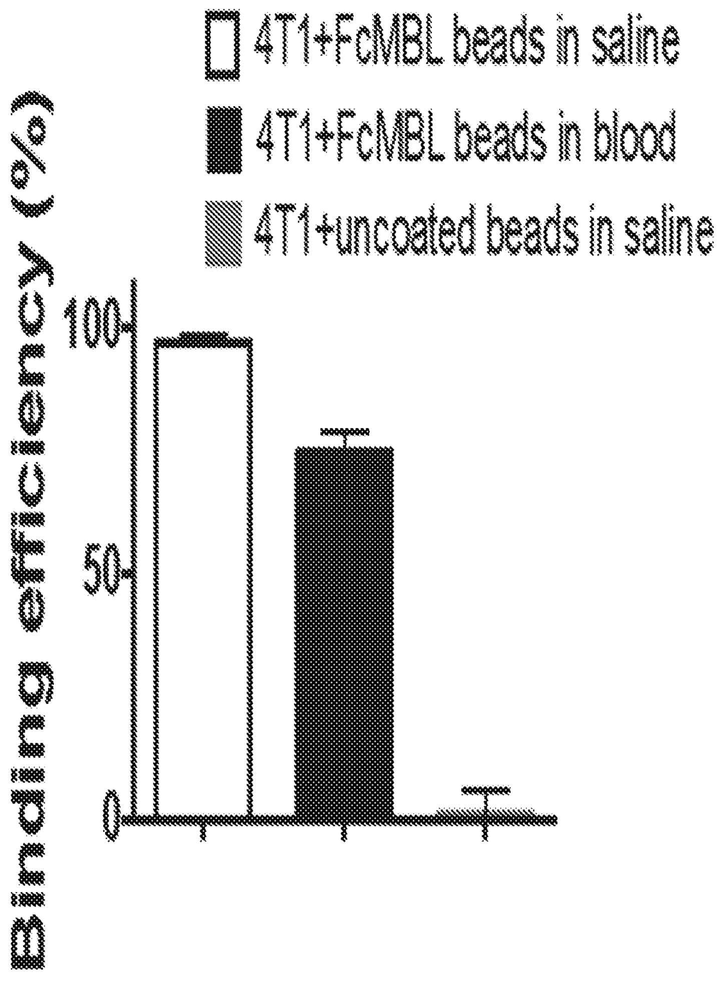
FIG. 4. The binding efficiency of FcMBL to 4T1 cells in saline and human whole blood. The FcMBL coated 1 μm magnetic particles bind to 4T1 cells in buffer and human whole blood with the efficiency of 97.2±1.6% and 74.6±4.2%, respectively. In comparison, the control magnetic particles without FcMBL did not show the binding affinity to 4T1 cells (1.5±4.4%).

Capturing Circulating Tumor Cells (4T1 Cells) in Blood Collected from Tumor Bearing Mice Using FcMBL Magnetic Particles To test the use of FcMBL to capture tumor cells circulating in blood of an animal, we implanted mouse 4T1 (mouse mammary carcinoma, cherry red expressing) breast tumor cells in mice and whole blood was obtained over time to assess the number of 4T1 cells that invaded into the bloodstream. Before validating the binding of FcMBL to 4T1 cells in vivo, a binding affinity test was carried out in vitro using 4T1 cells ($10^5$ cells/mL) suspended in saline with 5 mM calcium chloride and heparinized human whole blood. The 4T1 cell concentrations before and after performing a bead capture experiment were measured by a hemocytometer to calculate the binding efficiency of FcMBL-coated particles to 4T1 cells. The experimental results show that 1 μm FcMBL magnetic particles capture 97.2% and 74.6% of 4T1 cells spiked in saline and human whole blood, respectively, whereas control (uncoated) magnetic particles did not exhibit any binding (FIG. 4).

Figure 5:
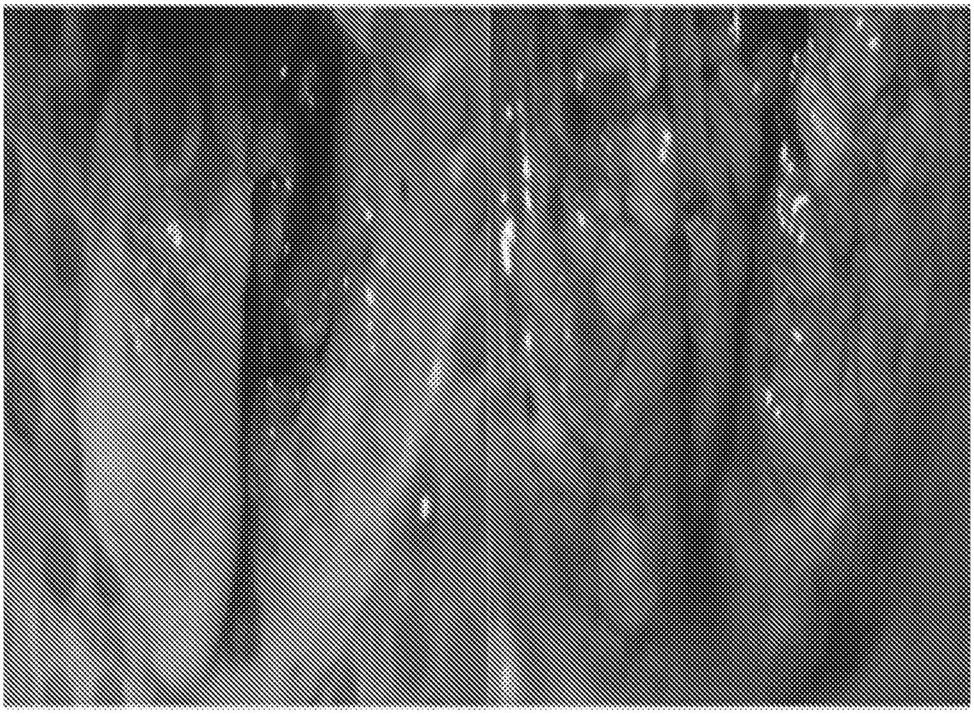
FIG. 5. The 4T1 cells implanted in mammary pads were metastasized to the lung after 20 days (left) and 30 days (right) post-implantation.
Figure 6:
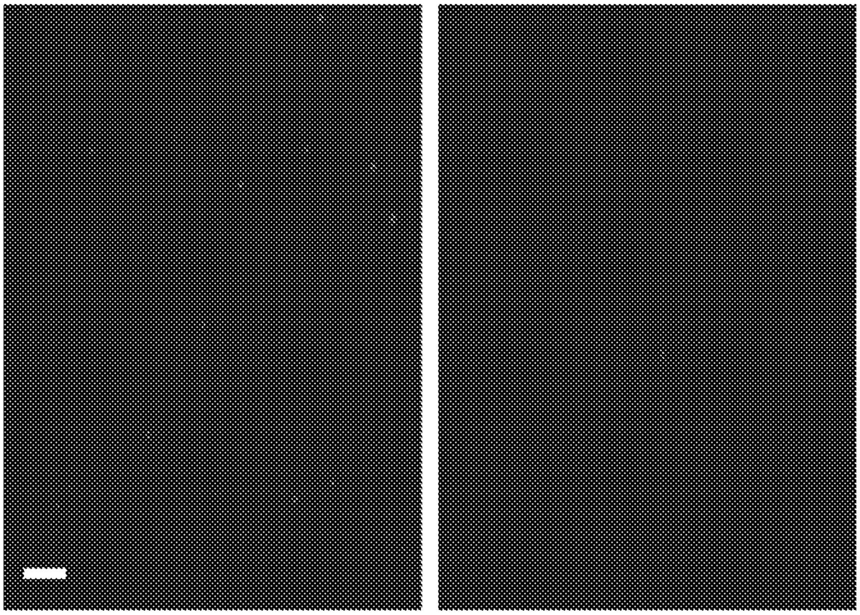
FIG. 6. The lysed mice blood (10 μL) containing 4T1 cells (cherry red expressing) was loaded into a hemocytometer and the number of 4T1 cells was counted. The 4T1 cells obtained from blood of the implanted tumor-bearing mice (30 days, left) were significantly depleted (over 90%, right) by magnetic separation with FcMBL-coated magnetic particles. Scale bar, 100 μm.

4T1 cells were implanted within mammary fat pads of mice. Methods for implantation are described in ref (2) and whole blood of the mice was collected after 10 days, 20 days and 30 days post-implantation. Metastasis of the implanted breast tumor to the lung was apparent after 20 days (FIG. 5) and the mice at 30 days post-implantation showed difficulty in breathing due to metastasized tumors in the lung.

At each time point (10, 20, 30 days post-implantation), whole blood (0.5~1.0 mL) was drawn from mice into heparin Vacutainer vials. The blood volume was measured to normalize the number of CTCs per unit volume of blood. 4T1 cells were not detected in blood collected at the 10 day time point; however, the blood collected after 20 days contained about ~102 4T1 cells/mL and the concentration increased up to about $10^6$ cells/mL at 30 days post-implantation. The blood drawn from mice was mixed with Roche RBC lysis buffer (Roche 10202500) to remove RBCs, and the pellets containing white blood cells and 4T1 cells were collected by centrifugation at 300 RCF for 5 min. The pellets were resuspended in 1 mL of saline with 5 mM calcium chloride and 15 μL of 1 μm FcMBL magnetic particles were then added and incubated for 20 min in a rotating mixer. The cells captured by FcMBL magnetic particles were removed by a magnetic separator and their numbers were counted using a hemocytometer to assess the binding efficiency of FcMBL magnetic particles to 4T1 cells. The experimental results show that over 90% of 4T1 cells circulating in mice blood were captured by FcMBL magnetic particles, which corresponds to the in vitro results described above.

Example 5

FcMBL Binding Affinity to Various Human Cancer Cells

Figure 7:
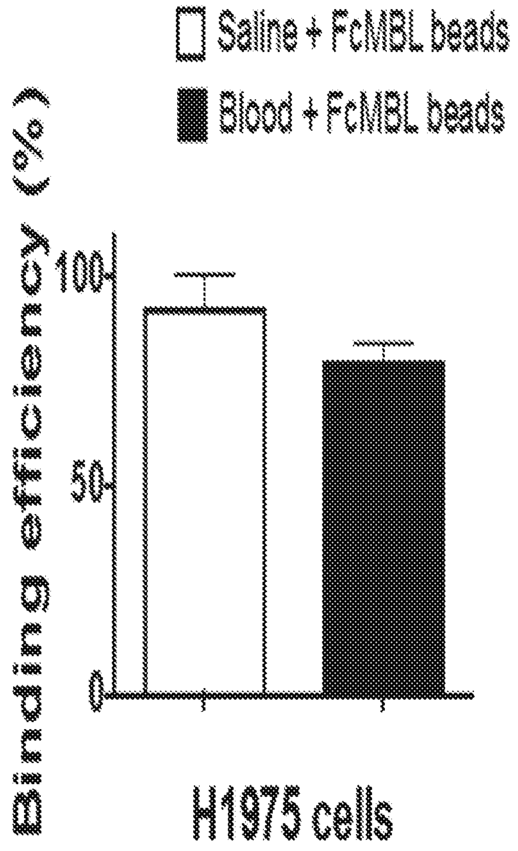
FIG. 7. The binding efficiency of H1975 cells to FcMBL-coated magnetic particles in saline with 5 mM calcium chloride and heparinized human whole blood. 90.2±5.0% and 80.6±2.4% of H1975 cells spiked in saline and human whole blood, respectively, were bound to 1 μm FcMBL magnetic particles.
Figure 9:
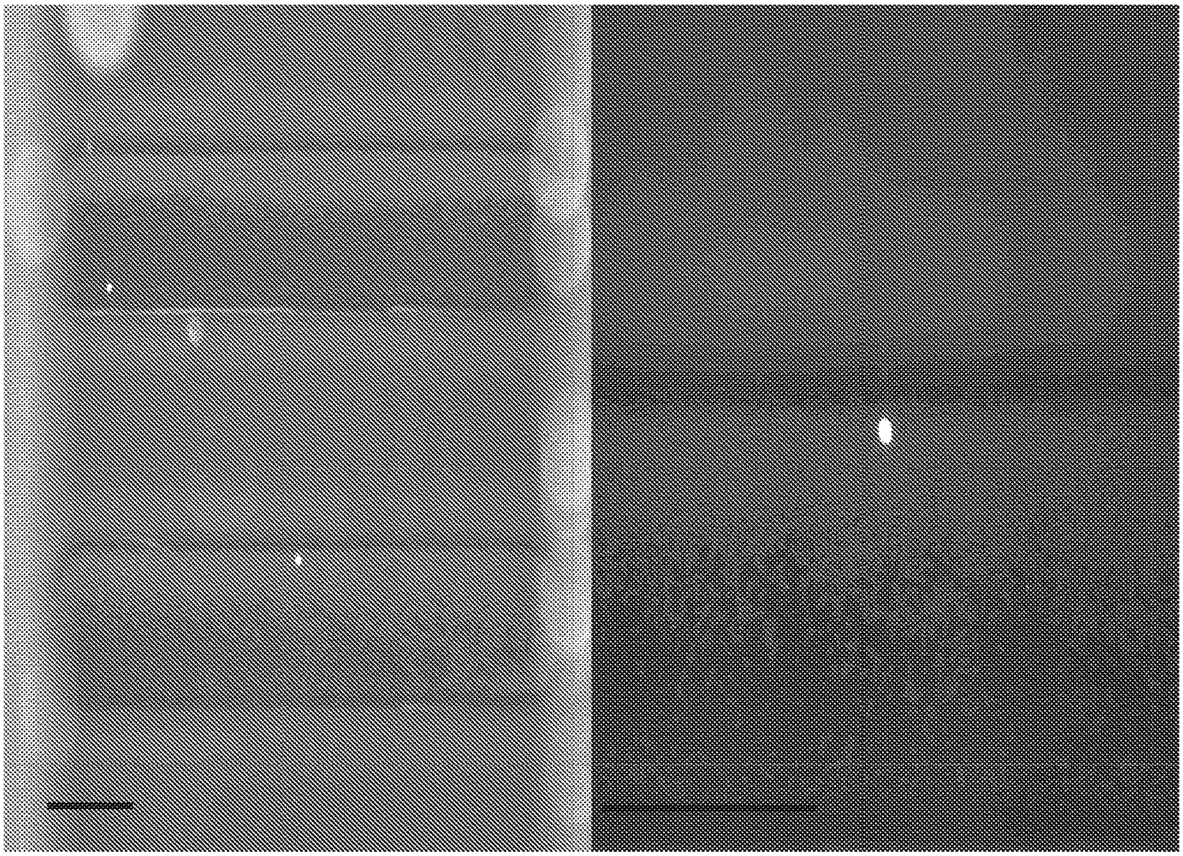
FIG. 9. 4T1 cells (cherry red fluorescence-expressing) spiked in blood were captured by FcMBL and isolated in the biospleen device. The cells isolated in the device were visualized and detected by a fluorescence microscope.

The binding ability of FcMBL to various human cancer cells, including H1975 (human lung adenocarcinoma), A549 (adenocarcinomic human alveolar basal epithelial cells), H358 (human bronchioloalveolar carcinoma cells), and H727 (human bronchial carcinoid cells) was tested in vitro. A binding test with H1975 was carried out using the methods described above. The experimental results (FIG. 7) show that 1 μm FcMBL magnetic particles could capture 90.2% and 80.6% of H1975 cells spiked in saline and human whole blood, respectively. Specific FcMBL binding was confirmed for all tested cancer cell types (FIG. 8). Weak binding was observed for MCF10a normal cells. These results demonstrate that the technology disclosed herein can be used to detect, capture and isolate CTCs from broad range of carcinomas.

REFERENCES

1. Baccelli, I. et al. (2013) Identification of a population of blood circulating tumor cells from breast cancer patients that initiates metastasis in a xenograft assay. Nat. Biotechnol. 31, 539.
2. Scher, H I. et al. (2009) Circulating tumour cells as prognostic markers in progressive, castration-resistant prostate cancer: a reanalysis of IMMC38 trial data. Lancet Oncol 10: 233-239.
3. Müller v. et al., (2005) Circulating tumor cells in breast cancer: correlation to bone marrow micrometastases, heterogeneous response to systemic therapy and low proliferative activity. Clin Cancer Res 11: 3678-3685.
4. Man, Y. et al. (2011) Currently Used Markers for CTC Isolation—Advantages, Limitations and Impact on Cancer Prognosis. J Clinic Experiment Pathol 1:102. doi: 10.4172/2161-0681.1000102.
5. Alix-Panabieres, C. & Pantel, K. (2013) Technologies for detection of circulating tumor cells:facts and vision. Lab Chip 14, 57.
6. Food and Drug Administration (2004) Medical devices; immunology and microbiology devices; classification of the immunomagnetic circulating cancer cell selection and enumeration system. Final rule. Fed Regist 69: 26036-26038.
7. Soysal, S. D. et al. (2013) EpCAM expression varies significantly and is differentially associated with prognosis in the luminal B HER2(+), basal-like, and HER2 intrinsic subtypes of breast cancer. Br. J. Cancer 108, 1480.
8. Gorges, T. M. et al. (2012) Circulating tumour cells escape from EpCAM-based detection due to epithelial-to-mesenchymal transition. BMC Cancer 12, 178.
9. Gold, B. et al. (2015) Do circulating tumor cells, exosomes, and circulating tumor nucleic acids have clinical utility? A report of the association for molecular pathology. J. Mol. Diagn. 17, 209.

10. Yu, M. et al. (2013) Circulating breast tumor cells exhibit dynamic changes in epithelial and mesenchymal composition. Science 339, 580

11. Wu S. et al. (2015) Classification of circulating tumor cells by epithelial-mesenchymal transition markers PLoS One. April 24; 10(4).

12. Kang, J H. et al. (2012) A combined micromagnetic-microfluidic device for rapid capture and culture of rare circulating tumor cells. Lab Chip. 2012 Jun. 21; 12(12): 2175-81.

13. Kang, J H. et al. (2014) An extracorporeal blood-cleansing device for sepsis therapy. Nature Medicine 20, 1211-1216

What is claimed is:

1. A method for capturing circulating tumor cells (CTCs) from a biological fluid of a subject, comprising; contacting the biological fluid with a C-type lectin molecule comprising a carbohydrate recognition domain (CRD) of mannose binding lectin attached to a surface.

2. The method of claim 1, wherein the surface is a bead, hollow fiber, porous scaffold, particle, or well.

3. The method of claim 1, wherein the surface is magnetic.

4. The method of claim 1, further comprising isolation of the captured CTCs.

5. The method of claim 4, wherein the isolation comprises passing the biological fluid containing captured CTCs through a microfluidic magnetic separation device.

6. The method of claim 1, wherein the CTCs express mannan carbohydrates on their cell surface.

7. The method of claim 1, wherein the CTCs express carbohydrates containing D-mannose and L-fucose onto their cell surface.

8. The method of claim 1, wherein the biological fluid is selected from a body fluid, such as whole blood, plasma, any cell-containing blood fraction, cerebrospinal fluid, bone marrow, cell sample, joint fluid, urine, tears or feces.

9. The method of claim 1, wherein the molecule further comprises the Fc region of an immunoglobulin.

10. The method of claim 9, wherein the molecule is FcMBL.

11. The method of claim 1, wherein the lectin molecule comprises at least 80% amino acid sequence identity to human mannose binding lectin and retains at least 80% of the wild-type carbohydrate binding activity.

12. The method of claim 1, further comprising assaying captured cells for CTC markers.

13. The method of claim 12, wherein the CTC markers are selected from GlcNAc, EpCAM, EphB4, HER2, EGFR, MUC-1, or a combination thereof.

14. A method for generating cancer vaccine, comprising:

(a) contacting a sample containing CTCs from a cancer patient with C-type lectin molecule comprising a carbohydrate recognition domain (CRD) of mannose binding lectin attached to a surface, whereby the lectin molecule binds the CTCs in the sample, thereby providing captured CTCs;

(b) isolating the captured CTCs;

(c) combining the isolated CTCs or a component thereof with an adjuvant to generate a CTC-immunogen thereby producing a cancer vaccine.

15. The method of claim 8, wherein the bone marrow or cell sample is obtained before transplantation.

16. The method of claim 1, wherein the C-type lectin molecule comprising a carbohydrate recognition domain (CRD) of mannose binding lectin (MBL) lacks a MBL collagen-like domain.

17. The method of claim 1, wherein the C-type lectin molecule is a carbohydrate recognition domain (CRD) of mannose binding lectin (MBL).

18. The method of claim 1, wherein the carbohydrate recognition domain (CRD) of mannose binding lectin (MBL) comprises the sequence of SEQ ID NO: 3.

19. The method of claim 1, wherein the carbohydrate recognition domain (CRD) of mannose binding lectin (MBL) does not activate complement or coagulation.

* * * * *